United States Patent
Rohwer et al.

(10) Patent No.: US 11,214,773 B2
(45) Date of Patent: Jan. 4, 2022

(54) ANTIBACTERIAL AND PROTECTIVE BACTERIOPHAGE FORMULATIONS AND METHODS FOR MAKING AND USING THEM

(71) Applicant: San Diego State University (SDSU) Foundation, San Diego, CA (US)

(72) Inventors: Forest Rohwer, San Diego, CA (US); Jeremy J. Barr, San Diego, CA (US)

(73) Assignee: San Diego State University (SDSU) Foundation, San Diego, CA (US)

( * ) Notice: Subject to any disclaimer, the term of this patent is extended or adjusted under 35 U.S.C. 154(b) by 254 days.

(21) Appl. No.: 15/762,908

(22) PCT Filed: Sep. 20, 2016

(86) PCT No.: PCT/US2016/052716
§ 371 (c)(1),
(2) Date: Mar. 23, 2018

(87) PCT Pub. No.: WO2017/053327
PCT Pub. Date: Mar. 30, 2017

(65) Prior Publication Data
US 2018/0273910 A1    Sep. 27, 2018

Related U.S. Application Data

(60) Provisional application No. 62/232,070, filed on Sep. 24, 2015.

(51) Int. Cl.
*C12N 7/00* (2006.01)
*A61P 31/04* (2006.01)
*A61K 35/76* (2015.01)
*C07K 14/005* (2006.01)

(52) U.S. Cl.
CPC ............... *C12N 7/00* (2013.01); *A61K 35/76* (2013.01); *A61P 31/04* (2018.01); *C07K 14/005* (2013.01); *C07K 2319/035* (2013.01); *C12N 2795/00021* (2013.01); *C12N 2795/00022* (2013.01); *C12N 2795/00031* (2013.01); *C12N 2795/00033* (2013.01); *Y02A 50/30* (2018.01)

(58) Field of Classification Search
None
See application file for complete search history.

(56) References Cited

U.S. PATENT DOCUMENTS

| | | |
|---|---|---|
| 2004/0039156 A1 | 2/2004 | Segal et al. |
| 2004/0161411 A1 | 8/2004 | Merril et al. |
| 2004/0161431 A1 | 8/2004 | Carlton et al. |
| 2015/0050717 A1 | 2/2015 | Collins et al. |

FOREIGN PATENT DOCUMENTS

| | | |
|---|---|---|
| EP | 1362910 A1 | 11/2003 |
| WO | 2007076101 A2 | 7/2007 |

OTHER PUBLICATIONS

Bar et al., BMC Biotechnology, 2008, 8:37. (Year: 2008).*
Yacoby et al., Antimicrobial Agents and Chemotherapy, Jun. 2006, 50(6):2087-2097. (Year: 2006).*
Barr et al., PNAS, Jun. 25, 2013, 110(26):10771-10776. (Year: 2013).*
Fraser et al., Journal of Molecular Biology, 2006, 359:496-507. (Year: 2006).*
Yamamoto et al., Biochemical and Biophysical Research Communications, 1999, 255:194-199). (Year: 1999).*
Sprinks, Supplementary European Search Report for EP 16849443, dated Feb. 11, 2019.
Copenheaver, Written Opinion of the International Search Report for PCT/US2016/052716, dated Nov. 10, 2016.
Copenheaver, International Search Report for PCT/US2016/052716, dated Nov. 10, 2016.
Regis, International Preliminary Report on Patentability for PCT/US2016/052716, dated Mar. 27, 2018.
Barr et al., "Bacteriophage adhering to mucus provide a non-host-derived immunity" PNAS, Jun. 25, 2013, v 110, n 26, p. 10771-10776.
Barr et al., "Subdiffusive motion of bacteriophage in mucosal surfaces increases the frequency of bacterial encounters" PNAS, Nov. 3, 2015, v 112, n 44, 13675-13680.
Byk et al., "Fully Synthetic Phage-Like System for Screening Mixtures of Small Molecules in Live Cells" Journal of Combinatorial Chemistry, 2010, v 12, n 3, p. 332-345.

* cited by examiner

Primary Examiner — Nicole Kinsey White
(74) Attorney, Agent, or Firm — Greer, Burns & Crain, Ltd.; Gregory P. Einhorn

(57) ABSTRACT

In alternative embodiments, provided are compositions comprising chemically or structurally modified bacteriophages of the genus *Caudovirales* having an exterior or outer surface comprising at least one heterologous carbohydrate binding domain (CBD) comprising a lectin or a plurality of additional homologous CBDs, or more CBDs than found on a comparable wild type (WT) bacteriophage.

18 Claims, 11 Drawing Sheets

FIG. 2A
FIG. 2B
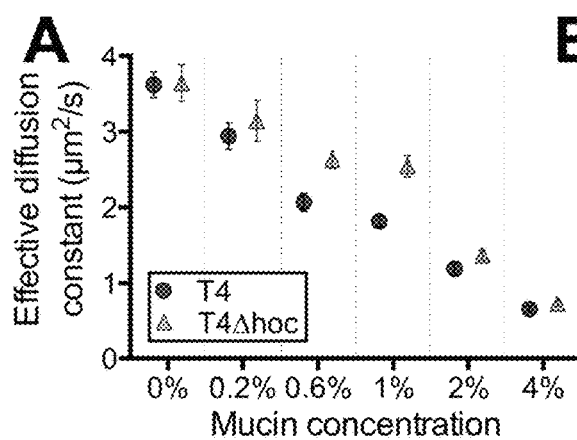
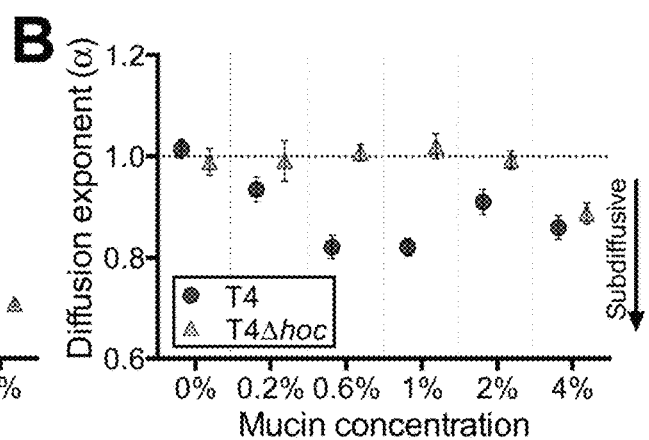

FIG. 5A
FIG. 5B
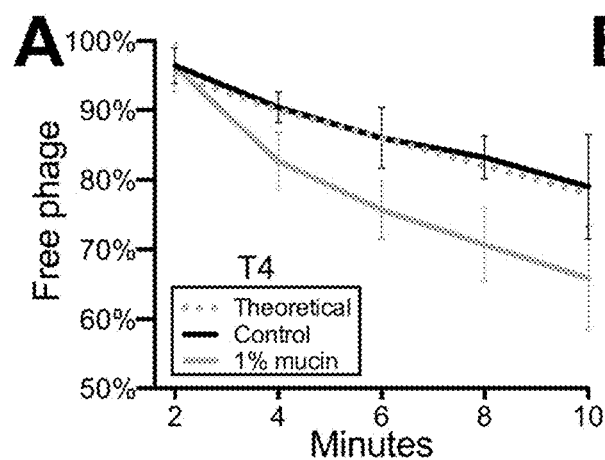
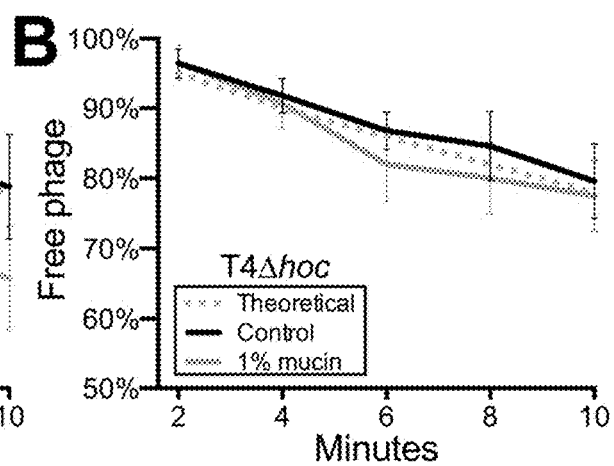

FIG. 6A
FIG. 6B
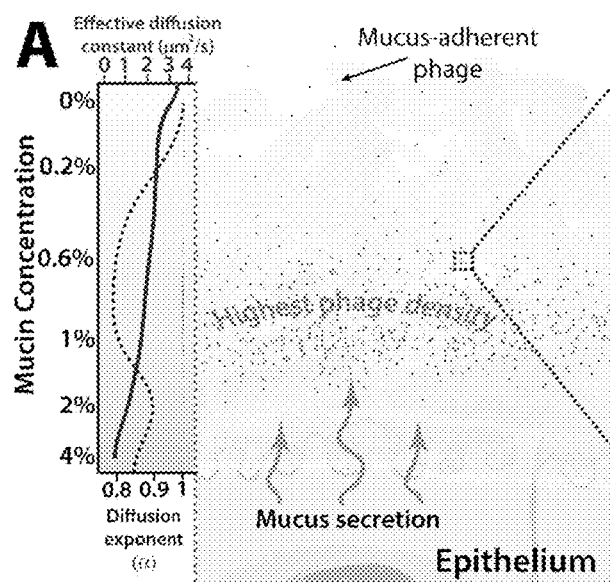
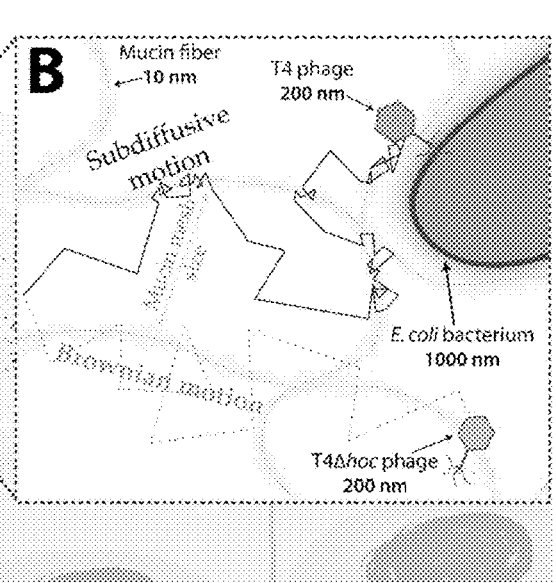

○ T4    • T4Δhoc    ----- Alpha = 1

ANTIBACTERIAL AND PROTECTIVE BACTERIOPHAGE FORMULATIONS AND METHODS FOR MAKING AND USING THEM

RELATED APPLICATIONS

This U.S. utility patent application is a national phase application claiming benefit of priority under 35 U.S.C. § 371 to International (PCT) Patent Application serial number PCT/US2016/052716, filed Sep. 20, 2016, which claims benefit of priority under 35 U.S.C. § 119(e) of U.S. provisional patent application Ser. No. (USSN) 62/232,070, filed Sep. 24, 2015. The aforementioned applications are expressly incorporated herein by reference in their entirety and for all purposes.

STATEMENT AS TO FEDERALLY SPONSORED RESEARCH

This invention was made with government support under grant numbers NIH R01: GM095384, and NIH R21: A1094534, awarded by the National Institute of General Medical, National Institutes of Health (NIH), DHHS. The government has certain rights in the invention.

TECHNICAL FIELD

This invention generally relates to medicine, infectious diseases, pharmacology and microbiology. In alternative embodiments, provided are compositions and methods for treating, ameliorating and preventing various infections, disorders and conditions in mammals, including genetically-predisposed and chronic disorders, where a microbial or bacterial flora is at least one causative or symptom-producing factor. In alternative embodiment, compositions and methods as provided herein are used to treat, prevent or ameliorate an infection, for example, an infection in the gastrointestinal tract, or bowel. In alternative embodiment, compositions and methods as provided herein comprise or comprise use of chemically or structurally modified, genetically engineered and/or synthetic bacteriophage, phagemids or phage-like particles for targeting and/or binding to specific infectious agents or pathogens, for example, bacteria, and in alternative embodiments the targeting or binding results in the bacteriophage, phagemids or phage-like particles preventing adherence of the bacteria to a mucosa and/or binding to and killing of the bacteria. In alternative embodiments, provided are compositions and methods for treating, ameliorating and/or preventing a condition comprising an abnormal, disrupted or pathological mucosal surface or mucus-covered epithelium, or a condition caused, modified or effected by an abnormal, disrupted or pathological microbiota, wherein optionally the infection or condition comprises a diarrhea, a colitis, obesity, diabetes, autism, a cystic fibrosis, a dysentery, a gastrointestinal infection, a gastrointestinal inflammation, a gastrointestinal dysbiosis, a gastrointestinal upset, a lung infection, a bacterial infection, a viral infection, a secondary infection, an inflammation, a mucus hypersecretion, or a dysbiosis.

BACKGROUND

Mucosal surfaces in all animals, mucosal surfaces provide critical immunological services by both protecting against invading bacterial pathogens and by supporting large communities of commensal microorganisms. Being exposed to the environment, mucosal surfaces are also the infection sites for many important bacterial diseases including acute diarrhea and cystic fibrosis in humans. This, combined with their accessibility, make mucosal surfaces attractive venues for phage therapy, i.e., the use of bacteriophages (phages) to treat and clear bacterial infections. Clinical success so far has been erratic. The complexities and dynamics of the mucus layer are rarely considered and the activity of phages therein are mostly unknown. Not surprisingly, phages effective in vitro do not consistently reduce mucosal bacterial host levels in vivo. An understanding of the interactions between phages and their bacterial hosts within the relevant physiological environment is critical for consistent success of phage therapy applications.

SUMMARY

In alternative embodiments, provided are chemically or structurally modified bacteriophages ("phages"), wherein the exterior (outer) surface of the bacteriophage comprises:
(a) at least one heterologous:
(i) carbohydrate binding domain (CBD),
(ii) a moiety or domain capable of binding to a component of a mucus,
optionally a mucus of or derived from: a mammalian mucus membrane, a gut, a urinary, a reproductive, an animal or an environmental mucus,
optionally capable of binding to a mucus or mucus-like macromolecule, a mucin, a fatty acid, a phospholipid, a cholesterol, an elastin, a glycoprotein, a mucin glycoprotein or glycan, a mucin protein, a humic acid, a cellulose, a chitin, a high molecular weight (MW) polysaccharide, an N-acetylgalactosamine, an N-acetylglucosamine, a fucose, a galactose, a sialic acid (N-acetylneuraminic acid) a mannose, or any combination thereof,
and optionally the moiety or domain capable of binding to a component of a mucus directs or targets the phage to a specific region of a mucosal surface that overlaps with a bacterial host range, and optionally the specific region comprises a mucosal surface basal layer, a mucosal surface apical layer, a mucosal surface lumen, a mucus layer, or a mucosal surface having a concentration of between about 0% to 1% mucin, or between about 1% to 5%, or a mucin concentration of between about 1% to 10%,
and optionally the moiety or domain capable of binding to a component of a mucus directs or that targets the phage to a specific region of a mucosal surface allows the phage to reside or concentrate or persist in a specific region of the mucosal surface that overlaps with a bacterial host range,
and optionally the phage is adapted to a physico-chemical environment of the mucus or specific region of a mucosal surface, and the physico-chemical environment optionally comprises: a pH range of between about 6 to 8, a pH range of between about 4 to 10, a pH range of between about 1 to 12, an ionic concentration of between about 1 mg to 1000 mg, an ionic concentration of between about 1 µg to 1000 g, an ionic concentration of between about 1 pgm to 1000 kg, a temperature change of between about 35° C. to 42° C., a temperature change of between about 25° C. to 55° C., or a temperature change of between about 1° C. to 99° C.;
(iii) moiety or domain capable of binding to a protein or peptide, a protein or peptide (optionally an antibody or antigen binding fragment thereof, an antigen, an immunogen, a tolerogen), a glycoprotein, a nucleic acid (optionally an RNA or a DNA), a lipid or cholesterol, a lipopolysaccharide, a mucopolysaccharide, a gel, a hydrogel, a complex fluid, or a combination thereof, or (iv) combination of any of (i) to (iii), wherein optionally the heterologous CBD is a bacteriophage carbohydrate binding domain (CBD), and optionally the heterologous CBD is a CBD derived from a different species, genus, family or order of bacteriophage; or the CBD is a mammalian or a human CBD, and optionally any of (i) to (iii) comprises or has structural homology to: a C-type lectin, a lectin, a bacteriodetes-associated carbohydrate-binding often N-terminal (BACON) domain, a Brefeldin A-Inhibited Guanine nucleotide-exchange factor for ADP-ribosylation factor (Big, optionally Big1, Big2, or Big3), a polycystic kidney disease domain (PKD), a Fibronectin type 3 homology domain (Fn3), a HYalin Repeat (HYR) domain, an Ig_2 domain, an immunoglobulin I-set domain, a carbohydrate-adherence domain, a mucus-binding protein, a glycan-binding protein, a protein-binding protein, a mucus-adhering protein or a mucus-adhering glycoprotein;

(b) additional homologous CBDs (more CBDs than found on a comparable wild type (WT) bacteriophage); or (c) a combination of (a) and (b).

In alternative embodiments, provided are genetically engineered bacteriophages ("phages"), wherein the bacteriophage genome is altered such that after reproduction in a host cell (optionally a bacterial host cell), or in an in vitro system, the exterior (outer) surface of the bacteriophage comprises:

(a) at least one non-bacteriophage carbohydrate binding domain (CBD), and optionally the CBD is a mammalian or a human CBD;

(b) at least one heterologous bacteriophage CBD, wherein optionally the heterologous CBD is a CBD from a different species, genus, family or order of bacteriophage;

(c) more CBDs than found on a wild type (WT) (comparable) bacteriophage; or (d) at least one moiety or domain capable of binding to a component of a mucus, optionally a mucus of or derived from: a mammalian mucus membrane, a gut, a urinary, a reproductive, an animal or an environmental mucus, optionally capable of binding to a mucus or mucus-like macromolecule, a mucin, a fatty acid, a phospholipid, a cholesterol, an elastin, a glycoprotein, a mucin glycoprotein or glycan, a mucin protein, a humic acid, a cellulose, a chitin, a high molecular weight (MW) polysaccharide, an N-acetylgalactosamine, an N-acetylglucosamine, a fucose, a galactose, a sialic acid (N-acetylneuraminic acid) a mannose, or any combination thereof, and optionally the moiety or domain capable of binding to a component of a mucus directs or targets the phage to a specific region of a mucosal surface that overlaps with a bacterial host range, and optionally the specific region comprises a mucosal surface basal layer, a mucosal surface apical layer, a mucosal surface lumen, a mucus layer, or a mucosal surface having a concentration of between about 0% to 1% mucin, or between about 1% to 5%, or a mucin concentration of between about 1% to 10%, and optionally the moiety or domain capable of binding to a component of a mucus directs or that targets the phage to a specific region of a mucosal surface allows the phage to reside or concentrate or persist in a specific region of the mucosal surface that overlaps with a bacterial host range, and optionally the phage is adapted to a physico-chemical environment of the mucus or specific region of a mucosal surface, and the physico-chemical environment optionally comprises: a pH range of between about 6 to 8, a pH range of between about 4 to 10, a pH range of between about 1 to 12, an ionic concentration of between about 1 mg to 1000 mg, an ionic concentration of between about 1 µg to 1000 g, an ionic concentration of between about 1 pgm to 1000 kg, a temperature change of between about 35° C. to 42° C., a temperature change of between about 25° C. to 55° C., or a temperature change of between about 1° C. to 99° C.;

(e) at least one moiety or domain capable of binding to a protein or peptide, a protein or peptide (optionally an antibody or antigen binding fragment thereof, an antigen, an immunogen, a tolerogen), a glycoprotein, a nucleic acid (optionally an RNA or a DNA), a lipid or cholesterol, a lipopolysaccharide, a mucopolysaccharide, a gel, a hydrogel, a complex fluid, or a combination thereof; or (f) any combination of (a) to (e), and optionally any of (a) to (e) comprises or has structural homology to: a C-type lectin, a lectin, a bacteriodetes-associated carbohydrate-binding often N-terminal (BACON) domain, a Brefeldin A-inhibited guanine nucleotide-exchange factor for ADP-ribosylation factor (Big, optionally Big1, Big2, or Big3), a polycystic kidney disease domain (PKD), a Fibronectin type 3 homology domain (Fn3), a HYalin Repeat (HYR) domain, an Ig_2 domain, an immunoglobulin I-set domain, a carbohydrate-adherence domain, a mucus-binding protein, a glycan-binding protein, a protein-binding protein, a mucus-adhering protein or a mucus-adhering glycoprotein.

In alternative embodiments, provided are synthetic bacteriophages ("phages") or phagemids, wherein the exterior (outer) surface of the bacteriophage or phagemid comprises:

(a) (i) at least one non-bacteriophage carbohydrate binding domain (CBD), wherein optionally the CBD is a mammalian or a human CBD;

(ii) at least one bacteriophage carbohydrate binding domain (CBD), (iii) at least as many CBDs found on a wild type (WT) (comparable) bacteriophage;

(iv) more CBDs than found on a wild type (WT) bacteriophage;

(v) at least one moiety or domain capable of binding to a component of a mucus, optionally a mucus of or derived from: a mammalian mucus membrane, a gut, a urinary, a reproductive, an animal or an environmental mucus, optionally capable of binding to a mucus or mucus-like macromolecule, a mucin, a fatty acid, a phospholipid, a cholesterol, an elastin, a glycoprotein, a mucin glycoprotein or glycan, a mucin protein, a humic acid, a cellulose, a chitin, a high molecular weight (MW) polysaccharide, an N-acetylgalactosamine, an N-acetylglucosamine, a fucose, a galactose, a sialic acid (N-acetylneuraminic acid) a mannose, or any combination thereof, and optionally the moiety or domain capable of binding to a component of a mucus directs or targets the phage or phagemid to a specific region of a mucosal surface that overlaps with a bacterial host range, and optionally the specific region comprises a mucosal surface basal layer, a mucosal surface apical layer, a mucosal surface lumen, a mucus layer, or a mucosal surface having a concentration of between about 0% to 1% mucin, or between about 1% to 5%, or a mucin concentration of between about 1% to 10%, and optionally the moiety or domain capable of binding to a component of a mucus directs or that targets the phage or phagemid to a specific region of a mucosal surface allows the phage or phagemid to reside or concentrate or persist in a specific region of the mucosal surface that overlaps with a bacterial host range, and optionally the phage is adapted to a physicochemical environment of the mucus or specific region of a mucosal surface, and the physicochemical environment optionally comprises: a pH range of between about 6 to 8, a pH range of between about 4 to 10, a pH range of between about 1 to 12, an ionic concentration of between about 1 mg to 1000 mg, an ionic concentration of between about 1 μg to 1000 g, an ionic concentration of between about 1 pgm to 1000 kg, a temperature change of between about 35° C. to 42° C., a temperature change of between about 25° C. to 55° C., or a temperature change of between about 1° C. to 99° C.;

(vi) at least one moiety or domain capable of binding to a protein or peptide, a protein or peptide (optionally an antibody or antigen binding fragment thereof, an antigen, an immunogen, a tolerogen), a glycoprotein, a nucleic acid (optionally an RNA or a DNA), a lipid or cholesterol, a lipopolysaccharide, a mucopolysaccharide, a gel, a hydrogel, a complex fluid, or a combination thereof; or (vii) any combination of (i) to (vi), and optionally any of (i) to (vi) comprises or has structural homology to: a C-type lectin, a lectin, a bacteriodetes-associated carbohydrate-binding often N-terminal (BACON) domain, a Brefeldin A-Inhibited Guanine nucleotide-exchange factor for ADP-ribosylation factor (Big, optionally Big1, Big2, or Big3), a polycystic kidney disease domain (PKD), a Fibronectin type 3 homology domain (Fn3), a HYalin Repeat (HYR) domain, an Ig_2 domain, an immunoglobulin I-set domain, a carbohydrate-adherence domain, a mucus-binding protein, a glycan-binding protein, a protein-binding protein, a mucus-adhering protein or a mucus-adhering glycoprotein; or (b) the synthetic bacteriophage or phagemid of (a), wherein the synthetic bacteriophage or phagemid is or comprises: a synthetic phage-like particle, a phage-like microsphere (see e.g., Byk et al., J. Comb. Chem. 2010 May 10; 12(3):332-45, or Khandadash, et al., The Open Optics Journal (2011) vol. 5 (Suppl 1-M3) 17-27), a bacteriophage particle, a prophage, a bacteriophage capsid, a protein shell, a nanoparticle, lytic phage, a temperate phage, a myoviridae, a siphoviridae, a podoviridae, a claudoviralaes, a DNA containing particle, an RNA containing particle, a replicative particle, a non-replicative particle or an equivalent thereof.

In alternative embodiments of the chemically or structurally modified bacteriophages, the genetically engineered bacteriophages, or the synthetic bacteriophages or phagemids as provided herein:

the bacteriophage or phagemid is or is derived from, or comprises the genome or substantial structural components of; or, the CBD, the homologous CBD or the heterologous CBD is, is derived from or has substantial structural homology to:

(i) a prokaryotic bacteriophage, optionally a bacterial or an Archaeal bacteriophage;

(ii) a prokaryotic bacteriophage of the order Caudovirales or Ligamenvirales;

(iii) a prokaryotic bacteriophage of the family Myoviridae, Siphoviridae, Podoviridae, Lipothrixviridae, Rudiviridae, Ampullaviridae, Bicaudaviridae, Clavaviridae, Corticoviridae, Cystoviridae, Fuselloviridae, Globuloviridae, Guttaviridae, Inoviridae, Leviviridae, Microviridae, Plasmaviridae or Tectivirus or a combination thereof (iv) a Bacteroidetes-infecting phage or a class I filamentous phage, or an F1 or an Fd filamentous bacteriophage;

(v) a bacteriophage Qβ virus-like particle; or (vi) an Enterobacteria phage T4, a lambda phage, an M13 Inoviridae phage, a crAss phage, or a phage capable of infecting a mammalian or a human gut.

In alternative embodiments of the chemically or structurally modified bacteriophages, the genetically engineered bacteriophages, or the synthetic bacteriophages or phagemids as provided herein:

(a) the at least one:

(i) non-bacteriophage carbohydrate binding domain (CBD), or mammalian or human CBD;

(ii) bacteriophage carbohydrate binding domain (CBD), (iii) CBD found on a wild type (WT) (comparable) bacteriophage;

(iv) moiety or domain capable of binding to a component of a mucus, optionally a mucus of or derived from: a mammalian mucus membrane, or a gut, a urinary, a reproductive, a lung, a respiratory, an ocular, an oral, a nasal, a sinus, an oropharyngeal, a stomach, a small intestine, a large intestine, an enteric, a bowel, a bladder an animal or an environmental mucus, and optionally the animal or environmental mucus is from or derived from: coral, aquaculture, dairy animals, feed animals, companion animals, farm animals, chicken, cow, sheep, pig, duck, fish, pets, veterinary animals, plants, or insects, optionally capable of binding to a mucus or mucus-like macromolecule, a mucin, a fatty acid, a phospholipid, a cholesterol, an elastin, a glycoprotein, a mucin glycoprotein or glycan, a mucin protein, a humic acid, a cellulose, a chitin, a high molecular weight (MW) polysaccharide, an N-acetylgalactosamine, an N-acetylglucosamine, a fucose, a galactose, a sialic acid (N-acetylneuraminic acid) a mannose, or any combination thereof;

(v) moiety or domain capable of binding to a protein or peptide, a protein or peptide (optionally an antibody or antigen binding fragment thereof, an antigen, an immunogen, a tolerogen), a glycoprotein, a nucleic acid (optionally an RNA or a DNA), a lipid or cholesterol, a lipopolysaccharide, a mucopolysaccharide, a gel, a hydrogel, a complex fluid, or a combination thereof; or (vi) any combination of (i) to (v), is part of, or is attached to, or comprises a phage tailspike protein;

(b) the CBD is entirely, or substantially, a synthetic or non-natural CBD, optionally an antibody or antigen binding domain that specifically binds to a carbohydrate;

(c) the CBD is or comprises a protein having a carbohydrate-binding-like fold, which optionally comprises a seven-stranded beta-sandwich, or optionally is or comprises an immunoglobulin-like binding domain, or a protein domain comprising a 2-layer sandwich of between 7 and 9 antiparallel β-strands arranged in two β-sheets;

(d) the CBD is or is derived from or has substantial structural identity (homology) to a mammalian or a human CBD;

(e) the bacteriophage is known or demonstrated to be toxic or lysogenic to a bacteria, or the bacteriophage is bacteriocidal or bacteriostatic, or the bacteriophage can treat, inhibit or prevent an infection, and optionally the bacteriophage is engineered to specifically bind to or target the bacteria, wherein optionally the bacteriophages are bacteriocidal or bacteriostatic to a gram negative bacteria or a gram positive bacteria, and optionally the bacteriophage is engineered to specifically bind to or target the gram negative bacteria or gram positive bacteria, and optionally the bacteria or infection is or is caused by an MSRA infection, a *Staphylococcus*, a *Staphylococcus aureus*, a *Clostridium*, a *Clostridium difficile*, a *Escherichia coli*, a *Shigella*, a *Salmonella*, a *Campylobacter*, a *Chloerae*, a *Bacillus*, a *Yersinia* or a combination thereof, and optionally the bacteriophage is engineered to specifically bind to or target the bacteria; or (f) the bacteriophage is made or identified by a process comprising: screening a plurality of bacteriophages for bacteriocidal or bacteriostatic properties against a bacteria of interest, and selecting the bacteriophages having a lysogenic or a bacteriocidal or bacteriostatic activity.

In alternative embodiments of the chemically or structurally modified bacteriophages, the genetically engineered bacteriophages, or the synthetic bacteriophages or phagemids as provided herein:

the CBD is, or is derived from, or has substantial structural identity (homology to):

(a) a protein having a carbohydrate-binding-like fold, which optionally comprises a seven-stranded beta-sandwich, or optionally is or comprises an immunoglobulin-like binding domain, or comprises a protein domain comprising a 2-layer sandwich of between 7 and 9 antiparallel β-strands arranged in two β-sheets;

(b) a CBD, optionally an antibody or antigen binding fragment thereof, capable of specifically binding to a tumor associated carbohydrate antigen (TACA); or (c) a carbohydrate-binding module family 1 (CBM1); a carbohydrate-binding module family 2 (CBM2); a carbohydrate-binding module family 3 (CBM3); a carbohydrate-binding module family 4 (CBM4); a carbohydrate-binding module family 5 (CBM5); a carbohydrate-binding module family 6 (CBM6); a carbohydrate-binding module family 7 (CBM7); a carbohydrate-binding module family 8 (CBM8); a carbohydrate-binding module family 9 (CBM9); a carbohydrate-binding module family 10 (CBM10); a carbohydrate-binding module family 11 (CBM11); a carbohydrate-binding module family 12 (CBM12); a carbohydrate-binding module family 13 (CBM13); a carbohydrate-binding module family 14 (CBM14); a carbohydrate-binding module family 15 (CBM15); a carbohydrate-binding module family 16 (CBM16); a carbohydrate-binding module family 17 (CBM17); a carbohydrate-binding module family 18 (CBM18); a carbohydrate-binding module family 19 (CBM19); a carbohydrate-binding module family 20 (CBM20); a carbohydrate-binding module family 21 (CBM21); a carbohydrate-binding module family 25 (CBM25); a carbohydrate-binding module family 27 (CBM27); a carbohydrate-binding module family 28 (CBM28); a carbohydrate-binding module family 33 (CBM33); a carbohydrate-binding module family 48 (CBM48); or, a carbohydrate-binding module family 49 (CBM49).

In alternative embodiments of the chemically or structurally modified bacteriophages, the genetically engineered bacteriophages, or the synthetic bacteriophages or phagemids as provided herein:

the bacteriophage or phagemid comprises, or contains within, or carries as a payload, a composition, wherein optionally the composition comprises:

(a) a drug; an antibiotic; a bacteriostatic agent; a cytotoxic agent; a nucleic acid; a phage genome; an siRNA or antisense nucleic acid; a carbohydrate; a protein or peptide; a lipid; an antibody; a small molecule; a label or tag; a fluorescent molecule; a radiopaque molecule; a magnetic particle; a radionucleotide; a CBD; a moiety or domain capable of binding to: a protein or peptide, a nucleic acid (optionally an RNA or a DNA), a lipid, a lipopolysaccharide or a mucopolysaccharide; or, any combination thereof; or (b) (i) a moiety or domain capable of binding to a component of a mucus, optionally capable of binding to a mucin, a fatty acid, a phospholipid, a cholesterol, an elastin, a glycoprotein, an N-acetylgalactosamine, an N-acetylglucosamine, a fucose, a galactose, a sialic acid (N-acetylneuraminic acid) a mannose, or any combination thereof; (ii) a moiety or domain capable of binding to a protein or peptide, a protein or peptide (optionally an antibody or antigen binding fragment thereof, an antigen, an immunogen, a tolerogen), a nucleic acid (optionally an RNA or a DNA), a lipid, a lipopolysaccharide, a mucopolysaccharide, or a combination thereof, or (iii) combination of any of (i) to (ii).

In alternative embodiments of the chemically or structurally modified bacteriophages, the genetically engineered bacteriophages, or the synthetic bacteriophages or phagemids as provided herein:

the exterior or outer surface of the bacteriophage or phagemid comprises, or has attached to or has adherent to (optionally covalently or non-covalently), or carries as a payload, a composition, wherein optionally the composition comprises:

(a) a drug; an antibiotic; a bacteriostatic agent; a cytotoxic agent; a nucleic acid; a phage genome; an siRNA or antisense nucleic acid; a carbohydrate; a protein or peptide; a lipid; an antibody; a small molecule; a label or tag; a fluorescent molecule; a radiopaque molecule; a magnetic particle; a radionucleotide; a CBD; a moiety or domain capable of binding to: a protein or peptide, a nucleic acid (optionally an RNA or a DNA), a lipid, a lipopolysaccharide or a mucopolysaccharide; or, any combination thereof; or (b) (i) a moiety or domain capable of binding to a component of a mucus, optionally capable of binding to a mucin, a fatty acid, a phospholipid, a cholesterol, an elastin, a glycoprotein, an N-acetylgalactosamine, an N-acetylglucosamine, a fucose, a galactose, a sialic acid (N-acetylneuraminic acid) a mannose, or any combination thereof; (ii) a moiety or domain capable of binding to a protein or peptide, a protein or peptide (optionally an antibody or antigen binding fragment thereof, an antigen, an immunogen, a tolerogen), a nucleic acid (optionally an RNA or a DNA), a lipid, a lipopolysaccharide, a mucopolysaccharide, or a combination thereof, or (iii) combination of any of (i) to (ii).

In alternative embodiments of the chemically or structurally modified bacteriophages, the genetically engineered bacteriophages, or the synthetic bacteriophages or phagemids as provided herein:

the bacteriophage or phagemid comprises, or has attached to or has adherent to, or carries as a payload, between 1 and about 500 CBD molecules, or between about 10 and 400 CBD molecules, or between about 20 and 300 CBD molecules, or about 2, 5, 10, 15, 20, 25, 30, 35, 40, 50, 60, 70, 80, 90, 100, 110, 120, 130, 140 or 150 or more CBD molecules, or wherein the bacteriophage or phagemid comprises, or has attached to or has adherent to, or carries as a payload, between 1 and about 500 molecules, or between about 10 and 400 molecules, or between about 20 and 300 molecules, or about 2, 5, 10, 15, 20, 25, 30, 35, 40, 50, 60, 70, 80, 90, 100, 110, 120, 130, 140 or 150 or more molecules, and optionally the molecule comprises:

(a) a drug; an antibiotic; a bacteriostatic agent; a cytotoxic agent; a nucleic acid; a phage genome; an siRNA or antisense nucleic acid; a carbohydrate; a protein or peptide; a lipid; an antibody; a small molecule; a label or tag; a fluorescent molecule; a radiopaque molecule; a magnetic particle; a radionucleotide; a CBD; a moiety or domain capable of binding to: a protein or peptide, a nucleic acid (optionally an RNA or a DNA), a lipid, a lipopolysaccharide or a mucopolysaccharide; or, any combination thereof; or (b) (i) a moiety or domain capable of binding to a component of a mucus, optionally capable of binding to a mucin, a fatty acid, a phospholipid, a cholesterol, an elastin, a glycoprotein, an N-acetylgalactosamine, an N-acetylglucosamine, a fucose, a galactose, a sialic acid (N-acetylneuraminic acid) a mannose, or any combination thereof; (ii) a moiety or domain capable of binding to a protein or peptide, a protein or peptide (optionally an antibody or antigen binding fragment thereof, an antigen, an immunogen, a tolerogen), a nucleic acid (optionally an RNA or a DNA), a lipid, a lipopolysaccharide, a mucopolysaccharide, or a combination thereof, or (iii) combination of any of (i) to (ii).

In alternative embodiments, provided herein are: a composition, a product of manufacture, a food, a drink, a nutraceutical, a formulation, a pharmaceutical or a pharmaceutical preparation comprising, or containing, or mixed with, or formulated with: a chemically or structurally modified bacteriophage as provided herein, or a genetically engineered bacteriophage as provided herein, or a synthetic bacteriophage or phagemid as provided herein, or a bacteriophage or phagemid as provided herein; and optionally the composition, product of manufacture, food, drink, nutraceutical, formulation, pharmaceutical or pharmaceutical preparation can comprise, contain, be manufactured as or formulated as or formulated at:

(a) a capsule, a tablet, a gel, a geltab, a liquid, a solid, an elixir, a spray, a powder, a suppository or an implant, a sachet, a lozenge, a freeze-dried composition, or an infant formula, (b) a per dose, or per serving, or per unit dosage at, or a total daily dose of: between about $10(1)$ (or $10^1$) and $10(20)$ plaque-forming units (PFUs), or between about $10(3)$ and $10(17)$ PFUs, or between about $10(5)$ and $10(12)$ PFUs, or between about $10(7)$ and $10(9)$ PFUs, (c) administration in vivo; or for enteral or parenteral administration, or for ophthalmic, topical, oral, intravenous (IV), intramuscular (IM), intrathecal, subcutaneous (SC), intracerebral, epidural, intracranial or rectal administration, or by inhalation, or (d) a particle, a nanoparticle, a liposome, a tablet, a pill, a capsule, a gel, a geltab, a liquid, a powder, a suspension, a syrup, an emulsion, a lotion, an ointment, an aerosol, a spray, a lozenge, an ophthalmic preparation, an aqueous or a sterile or an injectable solution, a patch (optionally a transdermal patch or a medicated adhesive patch), an implant, a dietary supplement, an ice cream, an ice, a yogurt, a cheese, an infant formula or infant dietary supplement, a pasteurized milk or milk product or milk-comprising product.

In alternative embodiments, the composition, product of manufacture, food, drink, nutraceutical, formulation, pharmaceutical or pharmaceutical preparation as provided herein, or a bacteriophage or phagemid as provided herein, further comprises, or contains, or is mixed with, or is formulated with or as:

a pharmaceutically acceptable excipient;

a flavoring or a sweetening agent, an aspartamine, a *stevia*, monk fruit, a sucralose, a saccharin, a cyclamate, a xylitol, a vanilla, an artificial vanilla or chocolate or strawberry flavor, an artificial chocolate essence, or a mixture or combination thereof;

a preservative, a benzoic acid, a potassium sorbate.

at least one probiotic or prebiotic, wherein optionally the prebiotic comprises an inulin, lactulose, extracts of artichoke, chicory root, oats, barley, various legumes, garlic, kale, beans or flacks or an herb;

at least one congealing agent, wherein optionally the congealing agent comprises an arrowroot or a plant starch, a powdered flour, a powdered potato or potato starch, an absorbant polymer, an Absorbable Modified Polymer (AMP®), EndoClot, Santa Clara, Calif.), and/or a corn flour or a corn starch;

at least one an anti-inflammatory agent, wherein optionally the inflammatory agent comprises or is an NSAID, a 4 or a 5-amino-salicylate, an olsalazine, a mesalazine, a sulfasalazine and/or a balsalazide or an equivalent thereof or a combination thereof;

an additive selected from one or more of a saline, a media, a defoaming agent, a surfactant agent, a lubricant, an acid neutralizer, a marker, a cell marker, a drug, an antibiotic, a contrast agent, a dispersal agent, a buffer or a buffering agent, a sweetening agent, a debittering agent, a flavoring agent, a pH stabilizer, an acidifying agent, a preservative, a desweetening agent and/or coloring agent, vitamin, mineral and/or dietary supplement, or a prebiotic nutrient;

and optionally the buffer or a buffering agent or the pharmaceutically acceptable excipient comprises an inorganic salt, a citric acid, a sodium chloride, a potassium chloride, a sodium sulfate, a potassium nitrate, a sodium phosphate monobasic, a sodium phosphate dibasic or combinations thereof;

and optionally the antacid comprises a calcium carbonate, a magnesium hydroxide, a magnesium oxide, a magnesium carbonate, an aluminum hydroxide, a sodium bicarbonate or a dihydroxyaluminum sodium carbonate; or any combination thereof.

In alternative embodiments, the composition, product of manufacture, food, drink, nutraceutical, formulation, pharmaceutical or pharmaceutical preparation as provided herein, or a bacteriophage or phagemid as provided herein, further comprises, or contains, or is mixed with, or is formulated with or as:

a delayed or gradual enteric release composition or formulation, and optionally the formulation comprises a gastro-resistant coating designed to dissolve at a pH of 7 in the terminal ileum, e.g., an active ingredient is coated with an acrylic based resin or equivalent, e.g., a poly(meth)acrylate, e.g. a methacrylic acid copolymer B, NF, such as EUDRAGIT S™ (Evonik Industries AG, Essen, Germany), which dissolves at pH 7 or greater, e.g., comprises a multimatrix (MINIX) formulation.

In alternative embodiments, provided herein are methods for:

treating, ameliorating and/or preventing a bacterial infection, defending, ameliorating and/or preventing a bacterial infection of mucosal surface or a mucus-covered epithelium, treating, ameliorating and/or preventing a bacterial infection in an individual having an infection or a condition comprising an abnormal, disrupted or pathological mucosal surface or mucus-covered epithelium, or a condition caused, modified or effected by an abnormal, disrupted or pathological microbiotia, or generating an immune response, wherein optionally the immune response is a humoral (antibody) response, a cell-mediated immune response, or a tolerogenic immune (suppressing) response, wherein optionally the infection or condition comprises a diarrhea, a colitis, obesity, diabetes, autism, a cystic fibrosis, a dysentery, a gastrointestinal infection, a gastrointestinal inflammation, a gastrointestinal dysbiosis, a gastrointestinal upset, a lung infection, a bacterial infection, a viral infection, a secondary infection, an inflammation, a mucus hypersecretion, or a dysbiosis, inhibiting bacterial adhesion to a mucosal surface or mucus-covered epithelium, comprising (a) administering or applying to an individual in need thereof:

(i) a composition, a product of manufacture, a food, a drink, a nutraceutical, a formulation, a pharmaceutical or a pharmaceutical preparation as provided herein; or (ii) a chemically or structurally modified bacteriophage as provided herein, a genetically engineered bacteriophage as provided herein, or a synthetic bacteriophage or phagemid as provided herein, or any bacteriophage or phagemid as provided herein, wherein optionally the individual is a mammal, and optionally the mammal is a human, or a human infant, and optionally an antacid or a buffer or buffering agent or a pharmaceutically acceptable excipient is administered before, during or after, or before and during, administration of the product of manufacture, food, drink, nutraceutical, formulation, pharmaceutical or pharmaceutical preparation of (a), and optionally sufficient amount of antacid, buffer or buffering agent is administered (optionally before, during or after, or before and during, administration) to raise the pH of the stomach in the individual to between about 2.5 and 7, or between about 3 and 6.5, or to about 5.0, 5.5, 6.0, 6.5, 6.8 or 7.0 (optionally these pH values reached before, during or after, or before and during, administration), and optionally the buffer or a buffering agent or the pharmaceutically acceptable excipient comprises an inorganic salt, a citric acid, a sodium chloride, a potassium chloride, a sodium sulfate, a potassium nitrate, a sodium phosphate monobasic, a sodium phosphate dibasic or combinations thereof, and optionally the antacid comprises a calcium carbonate, a magnesium hydroxide, a magnesium oxide, a magnesium carbonate, an aluminum hydroxide, a sodium bicarbonate or a dihydroxyaluminum sodium carbonate.

and optionally the method further comprises enhancing or increasing:

the concentration of the bacteriophage or phagemid in the epithelial mucus zone, or the adherence of a bacteriophage or phagemid on a mucus or in an epithelial mucus zone, the subdiffusion or subdiffusive rate of motion of the bacteriophage or phagemid in an epithelial mucus zone, or the encounter rates of the bacteriophage or phagemid with bacteria in mucus or in a mucus environment, by modifying or engineering the chemical or properties of the mucus to which the bacteriophage or phagemid is contacted with or administered to; or (b) the method of (a), further comprising administering a bacteria to the individual in need thereof, wherein optionally the bacterial is a probiotic or a therapeutic bacteria, and optionally the administered bacteria is a bacteria that is targeted for killing by the chemically or structurally modified bacteriophage as provided herein, the genetically engineered bacteriophage as provided herein, or the synthetic bacteriophage or phagemid as provided herein, or any bacteriophage or phagemid as provided herein, and optionally the administered bacteria is genetically modified to be resistant to the killing by the chemically or structurally modified bacteriophage as provided herein, the genetically engineered bacteriophage as provided herein, or the synthetic bacteriophage or phagemid as provided herein, or any bacteriophage or phagemid as provided herein, and optionally the resistance of the administered bacteria to the killing by the chemically or structurally modified bacteriophage as provided herein, the genetically engineered bacteriophage as provided herein, or the synthetic bacteriophage or phagemid as provided herein, or any bacteriophage or phagemid as provided herein, is genetically engineered by inserting a resistance gene or a resistance gene nucleic acid (resistance to killing by the phage or phagemid) in the bacteria, and optionally the genetically engineered resistance comprises inserting or placing a CRISPR cassette comprising CRISPR spacer or spacers into the engineered bacteria, optionally into the bacterial genome, wherein the CRISPR spacer or spacers confer the resistance, and optionally the CRISPR cassette comprises or is placed or inserted into or is contained within a plasmid or a vector, and optionally the bacteria upon which resistance is to be conferred is transformed with the CRISPR cassette, plasmid or vector, and optionally the bacteria is selected for a recombination event.

In alternative embodiments, provided herein are methods for:

concentrating a bacteriophage or phagemid in an epithelial mucus zone, or increasing adherence of a bacteriophage or phagemid on a mucus or in an epithelial mucus zone, increasing subdiffusion or subdiffusive motion of a bacteriophage or phagemid in an epithelial mucus zone, or increasing encounter rates of a bacteriophage or phagemid with a bacteria in mucus, or enhancing encounter rates with bacteria in a mucus environment, comprising:
(a) administering or applying to an individual in need thereof:
  (i) a composition, a product of manufacture, a food, a drink, a nutraceutical, a formulation, a pharmaceutical or a pharmaceutical preparation as provided herein; or
  (ii) a chemically or structurally modified bacteriophage as provided herein, a genetically engineered bacteriophage as provided herein, or a synthetic bacteriophage or phagemid as provided herein, or any bacteriophage or phagemid as provided herein,
    wherein optionally the individual is a mammal, and optionally the mammal is a human, or a human infant; or
(b) the method of (a), further comprising enhancing or increasing:
the concentration of the bacteriophage or phagemid in the epithelial mucus zone, or the adherence of a bacteriophage or phagemid on a mucus or in an epithelial mucus zone,
the subdiffusion or subdiffusive rate of motion of a bacteriophage or phagemid in an epithelial mucus zone, or
the encounter rates of the bacteriophage or phagemid with bacteria in mucus or in a mucus environment,
by modifying or engineering the chemical or properties of the mucus to which the bacteriophage or phagemid is contacted with or administered to.

In alternative embodiments, provided herein are methods for:

concentrating or focusing a bacteriophage or a phagemid in or to a specific region of a mucus, optionally an epithelial mucus, or to a specific mucus zone, or directing or engineering a bacteriophage or a phagemid to subdiffuse to a specific region of an epithelial mucus, or to a specific mucus zone, comprising:
(a) providing a chemically or structurally modified bacteriophage as provided herein, a genetically engineered bacteriophage as provided herein, or a synthetic bacteriophage or phagemid as provided herein, or any bacteriophage or phagemid as provided herein,
wherein the bacteriophage or phagemid comprises at least one moiety or binding domain capable of binding to a mucus or a component of a mucus such that the bacteriophage or phagemid is concentrated or focused in or to a specific region of an epithelial mucus, or to a specific mucus zone, or the bacteriophage or phagemid is directed to subdiffuse to a specific region of an epithelial mucus, or to a specific mucus zone, and
(b) contacting the bacteriophage or phagemid of (a) to the mucus,
wherein optionally the contacting is in vivo, and the contacting comprises administering or applying the bacteriophage or phagemid to an individual in need thereof.

In alternative embodiments, provided herein are methods for: matching, concentrating or focusing a bacteriophage or a phagemid to a specific bacterial pathogen colonization pattern, comprising:
(a) providing a chemically or structurally modified bacteriophage as provided herein, a genetically engineered bacteriophage as provided herein, or a synthetic bacteriophage or phagemid as provided herein, or any bacteriophage or phagemid as provided herein,
wherein the bacteriophage or phagemid comprises at least one moiety or binding domain capable of binding to a mucus or a component of a mucus such that the bacteriophage or phagemid is matched, concentrated or focused to a specific bacterial pathogen colonization pattern, and
(b) contacting the bacteriophage or phagemid of (a) to the mucus,
wherein optionally the contacting is in vivo, and the contacting comprises administering or applying the bacteriophage or phagemid to an individual in need thereof.

In alternative embodiments, provided herein are methods for: delivering a payload or a composition, or for labelling or coating a cell, comprising use of a chemically or structurally modified bacteriophage, a genetically engineered bacteriophage, or a synthetic bacteriophage or phagemid, comprising:
(a) contacting a cell with a chemically or structurally modified bacteriophage as provided herein, a genetically engineered bacteriophage as provided herein, or a synthetic bacteriophage or phagemid as provided herein, or any bacteriophage or phagemid as provided herein,
wherein the bacteriophage or phagemid is capable of specifically binding to the cells, and comprises or contains within or carries as a payload a composition,
wherein optionally the composition comprises a drug; an antibiotic; a bacteriostatic agent; a cytotoxic agent; a nucleic acid; a phage genome; an siRNA or antisense nucleic acid; a carbohydrate; a protein or peptide; a lipid; an antibody; a small molecule; a label or tag; a fluorescent molecule; a radiopaque molecule; a magnetic particle; a radionucleotide; a CBD; a moiety or domain capable of binding to: a protein or peptide, a nucleic acid (optionally an RNA or a DNA), a lipid, a lipopolysaccharide or a mucopolysaccharide; or, any combination thereof;
(b) the method of (a), wherein the contacting is in vitro or in vivo;
(c) the method of (a) or (b), wherein the chemically or structurally modified bacteriophage, the genetically engineered bacteriophage, or the synthetic bacteriophage or phagemid comprises:
  (i) a prokaryotic bacteriophage, optionally a bacterial or an Archaeal bacteriophage;
  (ii) a prokaryotic bacteriophage of the order Caudovirales or Ligamenvirales;

(iii) a prokaryotic bacteriophage of the family Myoviridae, Siphoviridae, Podoviridae, Lipothrixviridae, Rudiviridae, Ampullaviridae, Bicaudaviridae, Clavaviridae, Corticoviridae, Cystoviridae, Fuselloviridae, Globuloviridae, Guttaviridae, Inoviridae, Leviviridae, Microviridae, Plasmaviridae or Tectivirus or a combination thereof;

(iv) a Bacteroidetes-infecting phage or a class I filamentous phage, or an F1 or an Fd filamentous bacteriophage;

(v) a bacteriophage Qβ virus-like particle; or (vi) an Enterobacteria phage T4, a lambda phage, an M13 Inoviridae phage, a crAss phage, or a phage capable of infecting a mammalian or a human gut.

In alternative embodiments, provided herein are Uses of:

(a) a composition, a product of manufacture, a food, a drink, a nutraceutical, a formulation, a pharmaceutical or a pharmaceutical preparation as provided herein; or (b) a chemically or structurally modified bacteriophage as provided herein, a genetically engineered bacteriophage as provided herein, or a synthetic bacteriophage or phagemid as provided herein, or any bacteriophage or phagemid as provided herein, in the manufacture of a medicament for:

treating, ameliorating and/or preventing a bacterial infection, defending, ameliorating and/or preventing a bacterial infection of mucosal surface or a mucus-covered epithelium, treating, ameliorating and/or preventing a bacterial infection in an individual having an infection or a condition comprising an abnormal, disrupted or pathological mucosal surface or mucus-covered epithelium, or a condition caused, modified or effected by an abnormal, disrupted or pathological microbiotia, or generating an immune response, wherein optionally the immune response is a humoral (antibody) response, a cell-mediated immune response, or a tolerogenic immune (suppressing) response, wherein optionally the infection or condition comprises a diarrhea, a colitis, obesity, diabetes, autism, a cystic fibrosis, a dysentery, a gastrointestinal infection, a gastrointestinal inflammation, a gastrointestinal dysbiosis, a gastrointestinal upset, a lung infection, a bacterial infection, a viral infection, a secondary infection, an inflammation, a mucus hypersecretion, or a dysbiosis, concentrating phages in an epithelial mucus zone, or increasing adherence of a bacteriophage on a mucus or in an epithelial mucus zone, increasing subdiffusion of a bacteriophage in an epithelial mucus zone, or inhibiting bacterial adhesion to a mucosal surface or mucus-covered epithelium.

In alternative embodiments, provided herein are therapeutic formulations of:

(a) a composition, a product of manufacture, a food, a drink, a nutraceutical, a formulation, a pharmaceutical or a pharmaceutical preparation as provided herein; or (b) a chemically or structurally modified bacteriophage as provided herein, a genetically engineered bacteriophage as provided herein, or a synthetic bacteriophage or phagemid as provided herein, or any bacteriophage or phagemid as provided herein, for use in:

treating, ameliorating and/or preventing a bacterial infection, defending, ameliorating and/or preventing a bacterial infection of mucosal surface or a mucus-covered epithelium, treating, ameliorating and/or preventing a bacterial infection in an individual having an infection or a condition comprising an abnormal, disrupted or pathological mucosal surface or mucus-covered epithelium, or a condition caused, modified or effected by an abnormal, disrupted or pathological microbiotia, or generating an immune response, wherein optionally the immune response is a humoral (antibody) response, a cell-mediated immune response, or a tolerogenic immune (suppressing) response, wherein optionally the infection or condition comprises a diarrhea, a colitis, obesity, diabetes, autism, a cystic fibrosis, a dysentery, a gastrointestinal infection, a gastrointestinal inflammation, a gastrointestinal dysbiosis, a gastrointestinal upset, a lung infection, a bacterial infection, a viral infection, a secondary infection, an inflammation, a mucus hypersecretion, or a dysbiosis, concentrating phages in an epithelial mucus zone, or increasing adherence of a bacteriophage on a mucus or in an epithelial mucus zone, increasing subdiffusion of a bacteriophage in an epithelial mucus zone, or inhibiting bacterial adhesion to a mucosal surface or mucus-covered epithelium.

The details of one or more embodiments as provided herein are set forth in the accompanying drawings and the description below. Other features, objects, and advantages of the invention will be apparent from the description and drawings, and from the claims.

All publications, patents, patent applications cited herein are hereby expressly incorporated by reference for all purposes.

BRIEF DESCRIPTION OF THE DRAWINGS

The drawings set forth herein are illustrative of embodiments as provided herein and are not meant to limit the scope of the invention as encompassed by the claims.

FIG. 1B illustrates mucus-producing lung tissue culture cells seeded into the main channel of an exemplary chip, and FIG. 1C illustrates tissue culture cells in the main channel following perfusion for seven days, as described in detail in Example 2, below.

FIG. 1D illustrates an exemplary multiplex syringe pump and scaffold perfusing nine chips simultaneously, and FIG. 1E illustrates a close-up of an exemplary single chip bonded to a glass microscope slide with microfluidic tubing attached to the in and out ports; as described in detail in Example 2, below.

FIG. 2A graphically illustrates data showing diffusion rates (as the effective diffusion constant μm$^2$/second) of T4 and T4Δhoc phage in mucus using high-speed multiple particle tracking (MPT), where the diffusion of both phage types was observed across a range of physiological mucin concentrations, as described in detail in Example 2, below.

FIG. 2B graphically illustrates data showing the diffusion exponent (a) from MPT experiments for both T4 and T4Δhoc phage types at all mucin concentrations, as described in detail in Example 2, below.

FIG. 5A-B graphically illustrates data from an adsorption assay measuring the percentage of free phage remaining over a 10 min period in control (0%) and 1% mucin solutions, where theoretical values were calculated from the T4 phage adsorption constant (k)=2.4×10$^{-9}$ ml/min, phage concentration (2×10$^5$ ml$^{-1}$), and bacterial concentration (1×10$^7$ ml$^{-1}$): T4 phage (FIG. 5A) and T4Δhoc phage (FIG. 5B), as described in detail in Example 2, below.

FIG. 6A-B schematically illustrates Bacteriophage adherence to mucus (BAM) model with subdiffusion: FIG. 6A illustrates mucus layer components, where the Left panel illustrates qualitative representations of the effective diffusion constant (K) (solid blue line) and diffusion exponent (a) (dashed black line) for T4 phage from FIG. 2; and FIG. 6B illustrates transient binding of mucus-adherent phage to mucin glycoproteins, as described in detail in Example 2, below.

FIG. 8A T4 phage, and FIG. 8B T4Δhoc phage.

Like reference symbols in the various drawings indicate like elements.

Figure 1A:
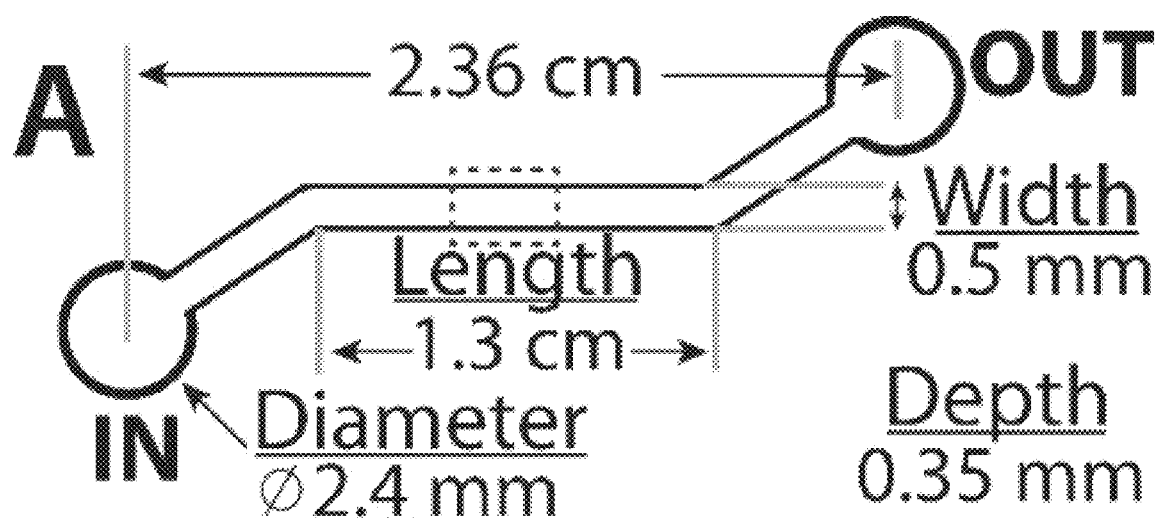
FIG. 1A schematically illustrates an exemplary microfluidic device (chip) design as provided herein that emulates the microenvironment of a mucus-producing epithelial surface experiencing constant fluid-flow across its surface, as described in detail in Example 2, below.
Figure 1B:
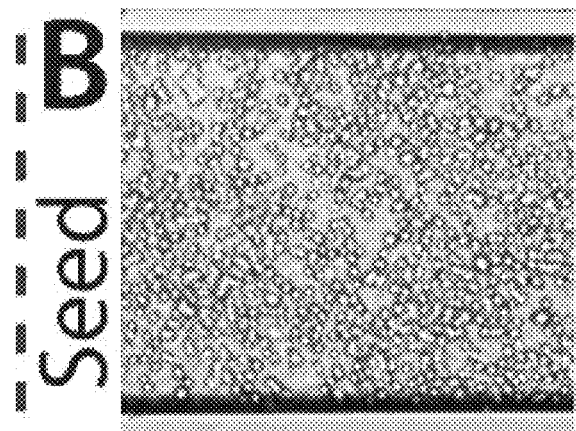
FIG. 1B-C illustrates an image of mucus-producing, human lung epithelial cells seeded into a channel of the exemplary microfluidic device as provided herein as illustrated in FIG. 1A, where the cells were allowed to attach to a glass surface.
Figure 1C:
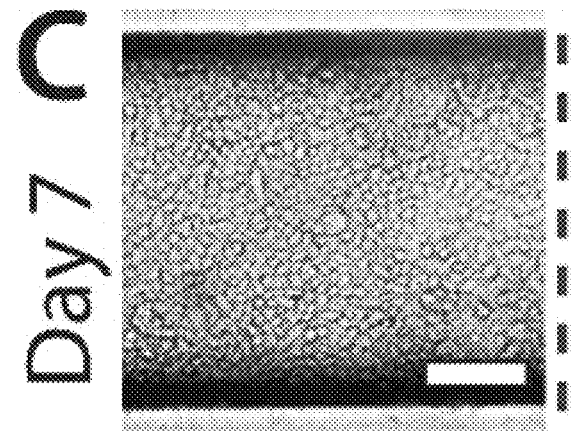
Figure 1D:
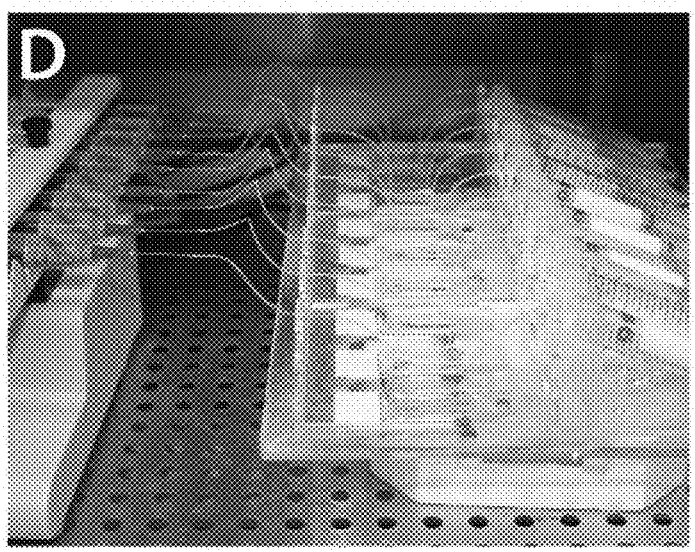
FIG. 1D-E schematically illustrate perfusion of tissue culture media through up to nine or the exemplary microfluidic devices (chips) simultaneously.
Figure 1E:
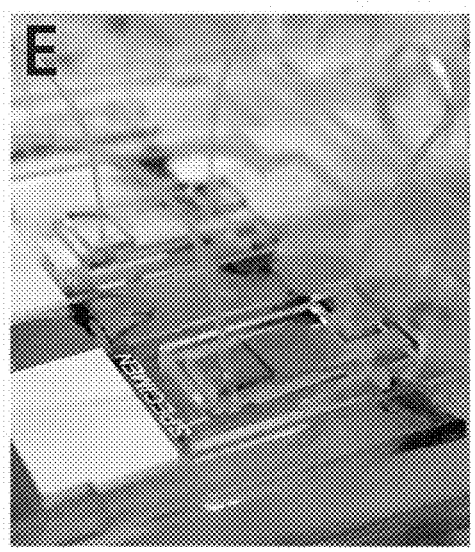

Reference will now be made in detail to various exemplary embodiments of the invention, examples of which are illustrated in the accompanying drawings. The following detailed description is provided to give the reader a better understanding of certain details of aspects and embodiments of the invention, and should not be interpreted as a limitation on the scope of the invention.

DETAILED DESCRIPTION

In alternative embodiments, provided are compositions and methods for treating, ameliorating and preventing various infections, disorders and conditions in mammals, including genetically-predisposed and chronic disorders, where a microbial or bacterial flora is at least one causative or symptom-producing factor; and optionally the microbe or bacterial is susceptible to lysis by a bacteriophage, or the bacteriophage has a microbiocidal, a bacteriocidal or bacteriostatic effect on the microbe or bacteria. In alternative embodiments, provided are products of manufacture, a food, a drink, a nutraceutical, a formulation, a pharmaceutical or a pharmaceutical preparation comprising a plurality of chemically or structurally modified, genetically engineered and/or synthetic bacteriophage, phagemids or phage-like particles as provided herein.

In alternative embodiments, compositions and methods of the invention are used to treat, prevent or ameliorate an infection, for example, an infection in the gastrointestinal tract, or bowel. In alternative embodiment, compositions and methods of the invention are used to specifically target and/or bind to a microbe or a bacteria that is pathogenic, or is associated with or completely or partially causative of an infection or a condition, including a condition caused, modified or effected by an abnormal, disrupted or pathological microbiotia (microbiome), including for example a diarrhea, a colitis, obesity, diabetes, autism, a cystic fibrosis, a dysentery, a gastrointestinal infection, a gastrointestinal inflammation, a gastrointestinal dysbiosis, a gastrointestinal upset, a lung infection, a bacterial infection, a viral infection, a secondary infection, an inflammation, a mucus hypersecretion, or a dysbiosis.

In alternative embodiment, compositions and methods of the invention are designed to target a particular microbe or bacteria by engineering a particular bacteriophage that has a microbiocidal, a bacteriocidal or bacteriostatic effect on the targeted microbe or bacteria. In alternative embodiments, compositions and methods of the invention comprise use of a bacteriophage specific for, or a bacteriophage engineered, designed or constructed to be (e.g., by recombinant technology) specific for, or a bacteriophage subunit responsible for specifically targeting, a particular infectious agent or pathogen, a microbe or a bacteria that is pathogenic, or is associated with or completely or partially causative of an infection or a condition, for example, bacteria.

In alternative embodiments, provided are compositions, e.g., a drug delivery agent, a liposome or a micelle, a hydrogel, a dendrimer, a particle or a microparticle, a powder, a nanostructure or a nanoparticle, capable of targeting a specific microbe or bacteria, where in alternative embodiments the specific targeting is effected by incorporation of a component of a bacteriophage specific for, or a bacteriophage designed or constructed to be (e.g., by recombinant technology) specific for, or a bacteriophage subunit responsible for specifically targeting, the specific microbe or bacteria, which can be a particular infectious agent or pathogen, a microbe or a bacteria that is pathogenic, or is associated with or completely or partially causative of an infection or a condition, for example, bacteria.

Probiotics and Prebiotics

In alternative embodiments, additives that are also included in a composition of the invention (e.g., a product of manufacture, food, drink, nutraceutical, formulation, pharmaceutical or pharmaceutical preparation), or a composition used to practice the invention, includes one or more prebiotics such as inulin, lactulose, extracts of artichoke, chicory root, oats, barley, various legumes, garlic, kale, beans or flacks and at times prebiotics may include herbs.

In alternative embodiments, additives may include beneficial (e.g., probiotic) flora components such as *Bacteroidetes, Firmicutes, Bacillus* (e.g., *Bacillus thurigiensis*) or any combination thereof. In alternative embodiments, cultured components are back to the flora to fortify or expand specific genus or species, e.g., *Bacteroidetes, Firmicutes, Bacillus* or *Bacillus thurigiensis*. Probiotics may at times be included as single cultured components. They would avoid multiply cultured components as they lose their implantation characteristics.

Preservatives, Cryoprotectants, Lyoprotectants

In alternative embodiments, to any composition of the invention, for example, a particle, a nanoparticle, a liposome, a tablet, a pill, a capsule, a gel, a geltab, a liquid, a powder, a suspension, a syrup, an emulsion, a lotion, an ointment, an aerosol, a spray, a lozenge, an ophthalmic preparation, an aqueous or a sterile or an injectable solution, a patch (optionally a transdermal patch or a medicated adhesive patch), an implant, a dietary supplement, an ice cream, an ice, a yogurt, a cheese, an infant formula or infant dietary supplement, a pasteurized milk or milk product or milk-comprising product, or a liquid preparation embodiment or candies, lollies, drinks and the like, there can be added various preservatives, cryoprotectants and/or lyoprotectants, including e.g., various polysaccharides or sugars (such as sucrose, fructose, lactose, mannitol), glycerol, polyethylene glycol (PEG), trehalose, glycine, glucose, dextran and/or erythritol. In alternative embodiments, other cryoprotectants that can be used are ethylene glycol, 1,2-Propanediol, Methylcelliosolve, Dimethyl Formamide, or Dimethylsulphoxide Methanol. In alternative embodiments the content of these cryoprotectants are between about 1% and about 50% but generally between about 5% and about 15% is adequate.

In alternative embodiments, a composition of the invention is frozen and/or is freeze-dried, or spray dried, or lyophilized, using any method known in the art. For example, a method for freeze-drying bacteriophage can be used as described by Puapermpoonsiri et al., Int J. Pharm. 2010 Apr. 15; 389(1-2): 168-75, who used sucrose or poly(ethylene glycol) 6000 to make bacteriophage-comprising freeze-dried cakes; or a method for making freeze-dried formulations of bacteriophage encapsulated in biodegradable microsphere, as described by Puapermpoonsiri et al., European J. Pharmaceutics and Biopharmaceutics, Vol. 72, Issue 1, 2009, Pgs 26-33; or methods for making stable bacteriophage compositions or matrices, as described e.g., by Murthy et al. WO2006047870 A1, or U.S. Pat. No. 8,309,077.

In alternative embodiments there are different types of final products that can be manufactured. In alternative embodiments a product or formulation of the invention is a liquid. In alternative embodiments a product or formulation of the invention is frozen and kept at e.g. minus 80 degrees for usage later given a cryoprotectant is added.

Biofilm Disrupting Compounds

In alternative embodiments, biofilm disrupting compounds added into a composition or formulation of the invention (e.g., a product of manufacture, food, drink, nutraceutical, formulation, pharmaceutical or pharmaceutical preparation), or used to practice a method of the invention. In alternative embodiments, in practicing the methods of the invention, biofilm disrupting compounds are administered before or during (co-administered), or co-formulated with (e.g., in a multilaminated tablet or capsule), or separately formulated, as the administered composition or formulation of the invention. In alternative embodiments, disrupting biofilms are used to separate from the colonic mucosa an adherent polysaccharide/DNA-containing layer, the so-called "biofilm".

In alternative embodiments, other biofilm disrupting components or agents also can be used, e.g., enzymes such as a deoxyribonuclease (DNase), a N-acetylcysteine, an auranofin, alginate lyase, glycoside hydrolase dispersin B; Quorum-sensing inhibitors e.g., ribonucleic acid III inhibiting peptide, *Salvadora persica* extracts, Competence-stimulating peptide, Patulin and penicillic acid; peptides-cathelicidin-derived peptides, small lytic peptide, PTP-7 (a small lytic peptide, see e.g., Kharidia (2011) J. Microbiol. 49(4): 663-8, Epub 2011 Sep. 2), Nitric oxide, neo-emulsions; ozone, lytic bacteriophages, lactoferrin, xylitol hydrogel, synthetic iron chelators, cranberry components, curcumin, silver nanoparticles, Acetyl-11-keto-β-boswellic acid (AKBA), barley coffee components, probiotics, sinefungin, S-adenosylmethionine, S-adenosyl-homocysteine, *Delisea* furanones, N-sulfonyl homoserine lactones and/or macrolide antibiotics or any combination thereof.

In alternative embodiments, biofilm disrupting components or agents are administered before and during the administration of a composition of this invention, e.g., as an antibacterial, in whatever format or formulation this may take place, for example, as a capsule.

In alternative embodiments, biofilm disrupting agents are added either before treatment and/or during and/or after treatment with a composition of the invention. In alternative embodiments, biofilm disrupting agents are used singly or in combination.

In alternative embodiments, biofilm disrupting agents include particular enzymes and degrading substances including in N-acetylcysteine, deoxyribonuclease (DNase). Others would include Alginate, lyase and Glycoside hydrolase dispersin, Ribonucleic-acid-III inhibiting peptide (RIP), *Salvadora persica* extracts, Competence-stimulating peptide (CSP) Patulin (PAT) and penicillic acid (PA)/EDTA, Cathelicidin-derived peptides, Small lytic peptide, PTP-7, Nitric oxide, Chlorhexidine, Povidone-iodine (PI), Nanoemulsions, Lytic bacteriophages, Lactoferrin/xylitol hydrogel, Synthetic iron chelators, Cranberry components, Curcumin, Acetyl-11-keto-boswellic acid (AKBA), Barley coffee (BC) components, silver nanoparticles, azithromycin, clarithromycin, gentamicin, streptomycin and also Disodium EDTA. Ozone insufflations of the colon can also be used to disrupt the biofilm.

Unit Dosage Forms and Formulations, Foods, and Delivery Vehicles

In alternative embodiments, a composition of the invention (e.g., a particle, a nanoparticle, a liposome, a tablet, a pill, a capsule, a gel, a geltab, a liquid, a powder, a suspension, a syrup, an emulsion, a lotion, an ointment, an aerosol, a spray, a lozenge, an ophthalmic preparation, an aqueous or a sterile or an injectable solution, a patch (optionally a transdermal patch or a medicated adhesive patch), an implant, a dietary supplement, an ice cream, an ice, a yogurt, a cheese, an infant formula or infant dietary supplement, a pasteurized milk or milk product or milk-comprising product) can be further processed by, e.g., spray-drying or equivalent, e.g., spray-drying in an inert gas or freeze-drying under similar conditions, thus ending up with a powdered product.

In alternative embodiments, a composition of the invention can be formulated for enteral or parenteral administration, e.g., to reach the systemic circulation, or for local delivery (e.g., for administration to skin, ears, teeth), as a topical for e.g., infections, as an inhalant, e.g., for inhalation of phages for the treatment of e.g., lung infections, as described e.g., by Ryan et al. J Pharm Pharmacol. 2011 October; 63(10):1253-64.

In alternative embodiments, a composition is manufactured, labelled or formulated as a liquid, a suspension, a spray, a gel, a geltab, a semisolid, a tablet, or sachet, a capsule, a lozenge, a chewable or suckable unit dosage form, or any pharmaceutically acceptable formulation or preparation. In alternative embodiments, a composition of the invention is incorporated into a food or a drink (e.g., a yogurt, ice cream, smoothie), a candy, sweet or lolly, or a feed, a nutritional or a food or feed supplement (e.g., liquid, semisolid or solid), and the like.

For example, bacteriophage used to practice the invention can be encapsulated as described, e.g., by Murthy et al. in US 2012-0258175 A1. A composition of the invention can be manufactured, labelled or formulated as an orally disintegrating tablet as described e.g., in U.S. Pat. App. Publication No. 20100297031. A composition of the invention can be a polyol/thickened oil suspension as described in U.S. Pat. Nos. 6,979,674; 6,245,740. A composition of the invention can be encapsulated, e.g., encapsulated in a glassy matrix as described e.g., in U.S. Pat. App. Publication No. 20100289164; and U.S. Pat. No. 7,799,341. A composition of the invention can be manufactured, labelled or formulated as an excipient particle, e.g., comprising a cellulosic material such as microcrystalline cellulose in intimate association with silicon dioxide, a disintegrant and a polyol, sugar or a polyol/sugar blend as described e.g., in U.S. Pat. App. Publication No. 20100285164. A composition of the invention can be manufactured, labelled or formulated as an orally disintegrating tablet as described e.g., in U.S. Pat. App. Publication No. 20100278930. A composition of the invention can be manufactured, labelled or formulated as a spherical particle, as described e.g., in U.S. Pat. App. Publication No. 20100247665, e.g., comprising a crystalline cellulose and/or powdered cellulose. A composition of the invention can be manufactured, labelled or formulated as a rapidly disintegrating solid preparation useful e.g. as an orally-disintegrating solid preparation, as described e.g., in U.S. Pat. App. Publication No. 20100233278. A composition of the invention can be manufactured, labelled or formulated as a solid preparation for oral application comprising a gum tragacanth and a polyphosphoric acid or salt thereof, as described e.g., in U.S. Pat. App. Publication No. 20100226866.

A composition of the invention can be manufactured, labelled or formulated using a water soluble polyhydroxy compound, hydroxy carboxylic acid and/or polyhydroxy carboxylic acid, as described e.g., in U.S. Pat. App. Publication No. 20100222311. A composition of the invention can be manufactured, labelled or formulated as a lozenge, or a chewable and suckable tablet or other unit dosage form, as described e.g., in U.S. Pat. App. Publication No. 20100184785.

A composition of the invention can be manufactured, labelled or formulated in the form of an agglomerate, as described e.g., in U.S. Pat. App. Publication No. 20100178349. A composition of the invention can be manufactured, labelled or formulated in the form of a gel or paste, as described e.g., in U.S. Pat. App. Publication No. 20060275223. A composition of the invention can be manufactured, labelled or formulated in the form of a soft capsule, as described e.g., in U.S. Pat. No. 7,846,475, or U.S. Pat. No. 7,763,276.

The polyols used in compositions of the invention can be micronized polyols, e.g., micronized polyols, e.g., as described e.g., in U.S. Pat. App. Publication No. 20100255307, e.g., having a particle size distribution ($d_{50}$) of from 20 to 60 µm, and a flowability below or equal to 5 s/100 g, or below 5 s/100 g.

In practicing the invention, a wide variation of bacteriophage can be administered, for example, in some aspects, a smaller dosage can be administered because phage (i.e., bacteriophage) can replication in the host, i.e., in the individual to which a composition of the invention is administered. In alternative embodiments, compositions of the invention, including phage of the invention, are formulated per dose, or per serving, or per unit dosage at, or at a total daily dose of: between about 10(1) (or $10^1$) and 10(20) plaque-forming units (PFUs), or between about 10(3) and 10(17) PFUs, or between about 10(5) and 10(12) PFUs, or between about 10(7) and 10(9) PFUs.

Gradual or Delayed Release Formulations

In alternative embodiments, the invention provides compositions formulated for delayed or gradual enteric release comprising at least one active agent (e.g., a composition, a formulation or a pharmaceutical preparation of the invention) formulated with a delayed release composition or formulation, coating or encapsulation. In alternative embodiments, formulations or pharmaceutical preparations of the invention are designed or formulated for delivery of active ingredient (e.g., a bacteriophage) into the distal small bowel and/or the colon. Thus, for this embodiment, it is important to allow the active ingredient to pass the areas of danger, e.g., stomach acid and pancreatic enzymes and bile, and reach undamaged to be viable in the distal small bowel and especially the colon. In alternative embodiments, a formulation or pharmaceutical preparation of the invention is a liquid formulation, a microbiota-comprising formulation of the invention and/or a frozen or a freeze-dried version thereof. In alternative embodiments, preferably for the encapsulated format, all are in powdered form.

In alternative embodiments, compositions of the invention are formulated for delayed or gradual enteric release using cellulose acetate (CA) and polyethylene glycol (PEG), e.g., as described by Defang et al. (2005) Drug Develop. & Indust. Pharm. 31:677-685, who used CA and PEG with sodium carbonate in a wet granulation production process.

In alternative embodiments, compositions of the invention are formulated for delayed or gradual enteric release using a hydroxypropylmethylcellulose (HPMC), a microcrystalline cellulose (MCC) and magnesium stearate, as described e.g., in Huang et al. (2004) European J. of Pharm. & Biopharm. 58: 607-614).

In alternative embodiments, compositions of the invention are formulated for delayed or gradual enteric release using e.g., a poly(meth)acrylate, e.g. a methacrylic acid copolymer B, a methyl methacrylate and/or a methacrylic acid ester, a polyvinylpyrrolidone (PVP) or a PVP-K90 and a EUDRAGIT® RL PO™, as described e.g., in Kuksal et al. (2006) AAPS Pharm. 7(1), article 1, E1 to E9.

In alternative embodiments, compositions of the invention are formulated for delayed or gradual enteric release as described in U.S. Pat. App. Pub. 20100239667. In alternative embodiments, the composition comprises a solid inner layer sandwiched between two outer layers. The solid inner layer can comprise a formulation or pharmaceutical preparation of the invention and one or more disintegrants and/or exploding agents, one of more effervescent agents or a mixture. Each outer layer can comprise a substantially water soluble and/or crystalline polymer or a mixture of substantially water soluble and/or crystalline polymers, e.g., a polyglycol. These can be adjusted in an exemplary composition of the invention to achieve delivery of the living components of an FMT distally down the bowel.

In alternative embodiments, compositions of the invention are formulated for delayed or gradual enteric release as described in U.S. Pat. App. Pub. 20120183612, which describes stable pharmaceutical formulations comprising active agents in a non-swellable diffusion matrix. In alternative embodiments, a formulation or pharmaceutical preparation of the invention is released from a matrix in a sustained, invariant and, if several active agents are present, independent manner and the matrix is determined with respect to its substantial release characteristics by ethylcellulose and at least one fatty alcohol to deliver bacteria distally.

In alternative embodiments, a formulation or pharmaceutical preparation of the invention is formulated for delayed or gradual enteric release as described in U.S. Pat. No. 6,284,274, which describes a bilayer tablet containing an active agent (e.g., an opiate analgesic), a polyalkylene oxide, a polyvinylpyrrolidone and a lubricant in the first layer and a second osmotic push layer containing polyethylene oxide or carboxy-methylcellulose.

In alternative embodiments, a formulation or pharmaceutical preparation of the invention is formulated for delayed or gradual enteric release as described in U.S. Pat. App. Pub. No. 20030092724, which describes sustained release dosage forms in which a nonopioid analgesic and opioid analgesic are combined in a sustained release layer and in an immediate release layer, sustained release formulations comprising microcrystalline cellulose, EUDRAGIT RSPO™ CAB-O-SIL™, sodium lauryl sulfate, povidone and magnesium stearate.

In alternative embodiments, a formulation or pharmaceutical preparation of the invention is formulated for delayed or gradual enteric release as described in U.S. Pat. App. Pub. 20080299197, describing a multi-layered tablet for a triple combination release of active agents to an environment of use, e.g., in the GI tract. In alternative embodiments, a multi-layered tablet is used, and it can comprise two external drug-containing layers in stacked arrangement with respect to and on opposite sides of an oral dosage form that provides a triple combination release of at least one active agent. In one embodiment the dosage form is an osmotic device, or a gastro-resistant coated core, or a matrix tablet, or a hard capsule. In these alternative embodiments, the external layers may contain biofilm dissolving agents and internal layers the living bacteria.

In alternative embodiments, a formulation or pharmaceutical preparation of the invention is formulated as multiple layer tablet forms, e.g., where a first layer provides an immediate release of a formulation or pharmaceutical preparation of the invention and a second layer provides a controlled-release of another (or the same) formulation or pharmaceutical preparation of the invention, or another active agent, as described e.g., in U.S. Pat. No. 6,514,531 (disclosing a coated trilayer immediate/prolonged release tablet), U.S. Pat. No. 6,087,386 (disclosing a trilayer tablet), U.S. Pat. No. 5,213,807 (disclosing an oral trilayer tablet with a core comprising an active agent and an intermediate coating comprising a substantially impervious/impermeable material to the passage of the first active agent), and U.S. Pat. No. 6,926,907 (disclosing a trilayer tablet that separates a first active agent contained in a film coat from a core comprising a controlled-release second active agent formulated using excipients which control the drug release, the film coat can be an enteric coating configured to delay the release of the active agent until the dosage form reaches an environment where the pH is above four).

In alternative embodiments, a formulation or pharmaceutical preparation of the invention is formulated for delayed or gradual enteric release as described in U.S. Pat. App. Pub. 20120064133, which describes a release-retarding matrix material such as: an acrylic polymer, a cellulose, a wax, a fatty acid, shellac, zein, hydrogenated vegetable oil, hydrogenated castor oil, polyvinylpyrrolidine, a vinyl acetate copolymer, a vinyl alcohol copolymer, polyethylene oxide, an acrylic acid and methacrylic acid copolymer, a methyl methacrylate copolymer, an ethoxyethyl methacrylate polymer, a cyanoethyl methacrylate polymer, an aminoalkyl methacrylate copolymer, a poly(acrylic acid), a poly(methacrylic acid), a methacrylic acid alkylamide copolymer, a poly(methyl methacrylate), a poly(methacrylic acid anhydride), a methyl methacrylate polymer, a polymethacrylate, a poly(methyl methacrylate) copolymer, a polyacrylamide, an aminoalkyl methacrylate copolymer, a glycidyl methacrylate copolymer, a methyl cellulose, an ethylcellulose, a carboxymethylcellulose, a hydroxypropylmethylcellulose, a hydroxymethyl cellulose, a hydroxyethyl cellulose, a hydroxypropyl cellulose, a crosslinked sodium carboxymethylcellulose, a crosslinked hydroxypropylcellulose, a natural wax, a synthetic wax, a fatty alcohol, a fatty acid, a fatty acid ester, a fatty acid glyceride, a hydrogenated fat, a hydrocarbon wax, stearic acid, stearyl alcohol, beeswax, glycowax, castor wax, carnauba wax, a polylactic acid, polyglycolic acid, a co-polymer of lactic and glycolic acid, carboxymethyl starch, potassium methacrylate/divinylbenzene copolymer, crosslinked polyvinylpyrrolidone, polyvinylalcohols, polyvinylalcohol copolymers, polyethylene glycols, non-crosslinked polyvinylpyrrolidone, polyvinyl acetates, polyvinylacetate copolymers or any combination. In alternative embodiments, spherical pellets are prepared using an extrusion/spheronization technique, of which many are well known in the pharmaceutical art. The pellets can comprise one or more formulations or pharmaceutical preparations of the invention, e.g., the liquid preparation embodiment.

In alternative embodiments, a formulation or pharmaceutical preparation of the invention is formulated for delayed or gradual enteric release as described in U.S. Pat. App. Pub. 20110218216, which describes an extended release pharmaceutical composition for oral administration, and uses a hydrophilic polymer, a hydrophobic material and a hydrophobic polymer or a mixture thereof, with a microenvironment pH modifier. The hydrophobic polymer can be ethylcellulose, cellulose acetate, cellulose propionate, cellulose butyrate, methacrylic acid-acrylic acid copolymers or a mixture thereof. The hydrophilic polymer can be polyvinylpyrrolidone, hydroxypropylcellulose, methylcellulose, hydroxypropylmethyl cellulose, polyethylene oxide, acrylic acid copolymers or a mixture thereof. The hydrophobic material can be a hydrogenated vegetable oil, hydrogenated castor oil, carnauba wax, candellia wax, beeswax, paraffin wax, stearic acid, glyceryl behenate, cetyl alcohol, cetostearyl alcohol or and a mixture thereof. The microenvironment pH modifier can be an inorganic acid, an amino acid, an organic acid or a mixture thereof. Alternatively, the microenvironment pH modifier can be lauric acid, myristic acid, acetic acid, benzoic acid, palmitic acid, stearic acid, oxalic acid, malonic acid, succinic acid, adipic acid, sebacic acid, fumaric acid, maleic acid; glycolic acid, lactic acid, malic acid, tartaric acid, citric acid, sodium dihydrogen citrate, gluconic acid, a salicylic acid, tosylic acid, mesylic acid or malic acid or a mixture thereof.

In alternative embodiments, a formulation or pharmaceutical preparation of the invention is a powder that can be included into a tablet or a suppository. In alternative embodiments, a formulation or pharmaceutical preparation of the invention can be a 'powder for reconstitution' as a liquid to be drunk or otherwise administered. In alternative embodiments, a formulation or pharmaceutical preparation of the invention is micro-encapsulated, formed into tablets and/or placed into capsules, especially enteric-coated capsules.

Buffers and Antacids

In alternative embodiments, in practicing the methods of the invention, buffers or antacids are administered before or during (co-administered), or co-formulated with a composition or formulation of the invention. For example, in alternative embodiments, a composition or formulation of the invention and a buffer or antacid are co-formulated, e.g., as multiple layer tablet form or as a multi-laminated tablet or capsule. In alternative embodiments of methods of the invention, buffers or antacids are separately formulated. In alternative embodiments, the antacid, buffer or buffering agent is administered (optionally before, during or after, or before and during, administration) to raise the pH of the stomach in the individual to between about 2.5 and 7, or between about 3 and 6.5, or to about 5.0, 5.5, 6.0, 6.5, 6.8 or 7.0 (optionally these pH values reached before, during or after, or before and during, administration). In alternative embodiments, the buffer or a buffering agent or the pharmaceutically acceptable excipient comprises an inorganic salt, a citric acid, a sodium chloride, a potassium chloride, a sodium sulfate, a potassium nitrate, a sodium phosphate monobasic, a sodium phosphate dibasic or combinations thereof. In alternative embodiments, the antacid comprises a calcium carbonate, a magnesium hydroxide, a magnesium oxide, a magnesium carbonate, an aluminum hydroxide, a sodium bicarbonate or a dihydroxyaluminum sodium carbonate.

Feeds, Drinks, Candies, Nutritional or a Food or Feed Supplements

In alternative embodiments, a formulation or pharmaceutical preparation of the invention is incorporated into a food, a feed, a candy (e.g., a lollypop or a lozenge) a drink, a nutritional or a food or feed supplement (e.g., liquid, semisolid or solid), and the like, as described e.g., in U.S. Pat. App. Publication No. 20100178413. In one embodiment, a formulation or pharmaceutical preparation of the invention is incorporated into (manufactured as) a beverage as described e.g., in U.S. Pat. No. 7,815,956. For example, a composition of the invention is incorporated into a yogurt, an ice cream, a milk or milkshake, a "frosty", "snow-cone", or other ice-based mix, and the like.

In alternative embodiments, a formulation or pharmaceutical preparation of the invention is a freeze-dried powder form added to a food, e.g., a yogurt, an ice cream, a milk or milkshake, a "frosty", "snow-cone", or other ice-based mix, and the like. In one form of this invention it can be kept in a lid-storage (e.g., of a yogurt or ice cream) such that when it is twisted the powder falls into the product or formulation (e.g., yoghurt or ice cream) and then it can be stirred so as not to have the powder ferment 'standing on the shelf'. Various flavourings can be added. In alternative embodiments, this is particularly important for administration of a composition of the invention, e.g., a wild type microbiota or a cultured bacteria, to a very young individual and/or a patient with autism or related disease or condition.

In alternative embodiments, these exemplary products are important when administered to children or babies who may have acquired various pathogenic or abnormal bacteria, e.g., *E. coli*, Clostridia or Disulfovibrio, e.g., as in autism.

Packaging

The invention provides compositions of the invention (e.g., a product of manufacture, food, drink, nutraceutical, formulation, pharmaceutical or pharmaceutical preparation), including preparations, formulations and/or kits, comprise combinations of ingredients, as described herein. In alternative embodiments, these combinations can be mixed and administered together, or alternatively, they can be an individual member of a packaged combination of ingredients, e.g., as manufactured in a separate package, kit or container; or, where all or a subset of the combinations of ingredients are manufactured in a separate package or container. In alternative aspects, the package, kit or container comprises a blister package, a clamshell, a tray, a shrink wrap and the like.

In one aspect, the package, kit or container comprises a "blister package" (also called a blister pack, or bubble pack). In one aspect, the blister package is made up of two separate elements: a transparent plastic cavity shaped to the product and its blister board backing. These two elements are then joined together with a heat sealing process which allows the product to be hung or displayed. Exemplary types of "blister packages" include: Face seal blister packages, gang run blister packages, mock blister packages, interactive blister packages, slide blister packages.

Blister packs, clamshells or trays are forms of packaging used for goods; thus, the invention provides for blister packs, clamshells or trays comprising a composition (e.g., a (the multi-ingredient combination of drugs of the invention) combination of active ingredients) of the invention. Blister packs, clamshells or trays can be designed to be non-reclosable, so consumers can tell if a package has already opened. They are used to package for sale goods where product tampering is a consideration, such as the pharmaceuticals of the invention. In one aspect, a blister pack of the invention comprises a moulded PVC base, with raised areas (the "blisters") to contain the tablets, pills, etc. comprising the combinations of the invention, covered by a foil laminate. Tablets, pills, etc. are removed from the pack either by peeling the foil back or by pushing the blister to force the tablet to break the foil. In one aspect, a specialized form of a blister pack is a strip pack. In one aspect, in the United Kingdom, blister packs adhere to British Standard 8404.

In one embodiment, the invention also provides a method of packaging where the compositions comprising combinations of ingredients of the invention are contained in-between a card and a clear PVC. The PVC can be transparent so the item (pill, tablet, geltab, etc.) can be seen and examined easily; and in one aspect, can be vacuum-formed around a mould so it can contain the item snugly and have room to be opened upon purchase. In one aspect, the card is brightly colored and designed depending on the item (pill, tablet, geltab, etc.) inside, and the PVC is affixed to the card using pre-formed tabs where the adhesive is placed. The adhesive can be strong enough so that the pack may hang on a peg, but weak enough so that this way one can tear open the join and access the item. Sometimes with large items or multiple enclosed pills, tablets, geltabs, etc., the card has a perforated window for access. In one aspect, more secure blister packs, e.g., for items such as pills, tablets, geltabs, etc. of the invention are used, and they can comprise of two vacuum-formed PVC sheets meshed together at the edges, with the informative card inside. These can be hard to open by hand, so a pair of scissors or a sharp knife may be required to open.

In one aspect, blister packaging comprises at least two or three or more components (e.g., is a multi-ingredient combination of the invention): a thermoformed "blister" which houses multi-ingredient combination of the invention, and then a "blister card" that is a printed card with an adhesive coating on the front surface. During the assembly process, the blister component, which is most commonly made out of PVC, is attached to the blister card using a blister machine. This machine introduces heat to the flange area of the blister which activates the glue on the card in that specific area and ultimately secures the PVG blister to the printed blister card. The thermoformed PVG blister and the printed blister card can be as small or as large as you would like, but there are limitations and cost considerations in going to an oversized blister card. Conventional blister packs can also be sealed (e.g., using an AERGO 8 DUO™, SCA Consumer Packaging, Inc., DeKalb Ill.) using regular heat seal tooling. This alternative aspect, using heat seal tooling, can seal common types of thermoformed packaging.

Blister Packaging

In alternative embodiments, combinations of ingredients of compositions of the invention, or combinations of ingredients for practicing methods of the invention, can be packaged alone or in combinations, e.g., as "blister packages" or as a plurality of packettes, including as lidded blister packages, lidded blister or blister card or packets or packettes, or a shrink wrap.

In alternative embodiments, laminated aluminium foil blister packs are used, e.g., for the preparation of drugs designed to dissolve immediately in the mouth of a patient. This exemplary process comprises having the drug combinations of the invention prepared as an aqueous solution(s) which are dispensed (e.g., by measured dose) into an aluminium (e.g., alufoil) laminated tray portion of a blister pack. This tray is then freeze-dried to form tablets which take the shape of the blister pockets. The alufoil laminate of both the tray and lid fully protects any highly hygroscopic and/or sensitive individual doses. In one aspect, the pack incorporates a child-proof peel open security laminate. In one aspect, the system give tablets an identification mark by embossing a design into the alufoil pocket that is taken up by the tablets when they change from aqueous to solid state. In one aspect, individual 'push-through' blister packs/packettes are used, e.g., using hard temper aluminium (e.g., alufoil) lidding material. In one aspect, hermetically-sealed high barrier aluminium (e.g., alufoil) laminates are used. In one aspect, any of the invention's products of manufacture, including kits or blister packs, use foil laminations and strip packs, stick packs, sachets and pouches, peelable and non-peelable laminations combining foil, paper, and film for high barrier packaging.

In alternative embodiments, any of the invention's multi-ingredient combinations or products of manufacture, including kits or blister packs, include memory aids to help remind patients when and how to take the drug. This safeguards the drug's efficacy by protecting each tablet, geltab or pill until it's taken; gives the product or kit portability, makes it easy to take a dose anytime or anywhere.

The invention will be further described with reference to the following examples; however, it is to be understood that the invention is not limited to such examples.

EXAMPLES

Example 1: Exemplary Phage Compositions of the Invention

This example provides exemplary processes for the synthesis, selection and adaptation of phages, phagemids and phage-like particles as provided herein.

Processes for the Selection and Adaptation of Exemplary Phages

In alternative embodiments, phage sequences from a mucosal environment or diseased mucosal surface, or physico-chemical environment are obtained, and so-called bacteriophage adherence to mucus (BAM) domains are identified and utilized for a personalized therapy or targeted approach to specific mucosal surfaces. BAM phages are enriched and isolated from mucus through selective culturing processes including but not limited to; culturing a specific bacterial host in a mucus across a range of concentrations and physic-chemical environments defined above, including the addition of specific phage populations, addition of environmental viral preps, patient viral preps, and culturing of mucus, bacterial host, and phage/viral preps over between about 1 to 100 generations, between about 1 to 100,000 generations, between about 1-100,000,000,000 generations, or between about 1 to $10^{100}$ generations.

In alternative embodiments, BAM phages are adapted or optimized to change their interactions with mucus through selective rounds of evolution/generations with a target bacterial host in a mucus layer, that includes but is not limited to; tissue culture, animal models, in vivo systems, microfluidic systems, model systems, culturing with mucus, and simulated mucus environments.

In alternative embodiments, BAM domains are genetically engineered to change their interactions with mucus through techniques including but not limited to: genetic manipulation, CRISPR techniques, DNA synthesis, DNA cloning, reverse transcriptase, diversity-generating retroelements, mutagenesis, radiation, carcinogens, homologous recombination, recombination, modular inserts, protein-protein interactions, protein-glycan interactions and the like.

In alternative embodiments, BAM domains are engineered or added to phage particles, phagemids, prophages and equivalents, e.g., temperate phages, prophages, incomplete temperate phages, viral capsid sequences, viral sequences, bacterial strains containing integrated phages or viral-like sequences, integrated viral sequences, temporary or potential bacterial hosts for phage infection and generation of engineered BAM phages, massive bacterial or yeast or eukaryotic or Archaeal or a viral display library of BAM domains.

In alternative embodiments, bacterial strains are engineered or selected for BAM domains on applications including but not limited to; probiotics, prophylactic therapies, phage therapy, corrective microbiome therapies, mucosal disease treating microorganisms. In alternative embodiments, BAM domains are engineered, selected, adapted, added, optimized, enriched, isolated, utilized using a mathematical approach that includes but is not limited to; mathematical models, Markov model, random forest, artificial neural networks.

Processes and Methods for the Synthesis of BAM Phages

In alternative embodiments, BAM phages are synthesized from DNA or RNA or nucleic acid. BAM phages can be synthesized in vitro using chemical, enzymatic, biological processes, including but not limited to genetically engineered techniques discussed above.

In alternative embodiments, BAM domains are expressed in bacterial host expression systems including but not limited to bacterial expression systems, yeast expression systems, eukaryotic expression systems, Archaeal expression systems, viral expression systems, synthetic expression systems, enzymatic expression systems, chemical expression systems. BAM domain expression systems are used to synthesize domains that interact with mucus for the generation of particles that include but are not limited to; phage, viruses, nanotechnology, nanoparticles, microparticles, picoparticles, drugs, drug delivery, macromolecules, chemicals, enzymes, phospholipids, nutrients, lipid vesicles, liposomes, microbial cells, microorganisms, nano-spheres, micro-spheres, pico-spheres, phage ghosts, vaccines, antibodies, phagesins, tailsin, holins, lysins, immune cells, eukaryotic cells, cancer cells, infectious diseases, parasites and the like.

In alternative embodiments, BAM domains are BAM domains are engineered on particles to induce an immune response for vaccines.

In alternative embodiments, BAM domains are BAM domains are engineered on particles to induce transepithelial uptake or transcytosis.

Example 2: Exemplary Methods of the Invention

This example provides data demonstrating the efficacy of the invention, and, while the invention is not limited by any particular mechanism of action, this example provides exemplary mechanisms by which aspects of the invention provide antibacterial protection to an individual in need thereof.

Bacteriophages (phages) defend mucosal surfaces against bacterial infections. However, their complex interactions with their bacterial hosts and with the mucus-covered epithelium remain mostly unexplored. Our previous work demonstrated that T4 phage with Hoc (Highly immunogenic outer capsid protein) proteins exposed on their capsid adhered to mucin glycoproteins and protected mucus-producing tissue culture cells in vitro. On this basis we proposed our bacteriophage adherence to mucus (BAM) model of immunity, whereby phages adhere to the mucosal surfaces of animals and provide a non-host-derived layer of immunity.

Here, to test this model, we developed a microfluidic device (chip) that emulates a mucosal surface experiencing constant fluid-flow and mucin secretion dynamics. Using mucus-producing human cells and E. coli in the chip, we observed similar accumulation and persistence of mucus-adherent T4 phage and non-adherent T4Δhoc phage in the mucus. Nevertheless, T4 phage reduced bacterial colonization of the epithelium >4000-fold compared to T4Δhoc phage. This suggests that phage adherence to mucus increases encounters with bacterial host encounters by some other mechanism.

Phages are traditionally thought to be completely dependent on normal diffusion, driven by random Brownian motion, for host contact. We demonstrated that T4 phage particles displayed subdiffusive motion in mucus while T4Δhoc particles displayed normal diffusion. Experiments and modeling indicate that subdiffusion is a more efficient search strategy for phages when bacterial concentration is low. By concentrating phages in an optimal mucus zone, subdiffusion increases their host encounters and antimicrobial action. Our revised BAM model proposes that the fundamental mechanism of mucosal immunity is subdiffusion resulting from adherence to mucus. These findings provide the basis for the engineered phages as provided herein, including methods for manipulating and personalizing the mucosal microbiome as provided herein.

Bacteriophage (phage) are viruses that infect and kill bacteria. Being inanimate, phages rely on diffusion to search for bacterial prey. Here we demonstrate that a phage that adheres weakly to mucus exhibits subdiffusive motion, not normal diffusion, in mucosal surfaces. Supporting theory and experiments revealed that subdiffusion is a more efficient search strategy for phages when bacterial concentration is low. To the best of our knowledge, no other predator has been shown to effectively utilize a subdiffusive search strategy. Mucosal surfaces are vulnerable to infection. Mucus-adherent phages reduce bacterial infection of life-like mucosal surfaces more effectively than non-adherent phages. These findings provide a basis for engineering adherent phages to manipulate mucosal surface microbiomes for protection from infection and other purposes.

Results

Dynamic Mucus Environment on a Chip.

Deciphering the role of phage-bacterial-host interactions in mucosal infections has been hindered by the lack of a reproducible, dynamic, and life-like experimental mucosal surface. To fill this gap we developed a microfluidic device (chip) that emulates the microenvironment of a mucus-producing epithelial surface experiencing constant fluid-flow across its surface. We then employed these chips to study the ability of phages to persist in the mucus layer and to protect the epithelium from infection. The chips were made of poly(dimethylsiloxane) (PDMS) and consisted of a single microfluidic channel, with in and out ports, attached to a glass microscope slide (FIG. 1A). Mucus-producing, human lung epithelial cells were seeded into the channel and allowed to attach to the glass surface. Tissue culture media was then perfused through up to nine chips simultaneously for seven days prior to all experiments. We maintained a lower flow rate (40 µl h$^{-1}$) for the first four days to ensure the establishment of an intact monolayer, then increased the flow rate to 100 µl h$^{-1}$ (0.02 dyne cm$^{-2}$) for the following three days and for all experiments to mimic the in vivo fluid flow and shear stresses (13, 14). These conditions consistently provided a confluent epithelial cell layer that exhibited mucus secretion and turnover dynamics (FIGS. 1B-E).

Interactions Between Bacteria, Phages, and Mucus on a Chip.

Figure 1F:
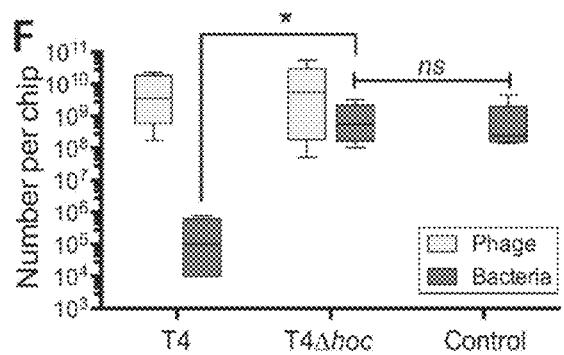
FIG. 1F graphically illustrates data from a Phage therapy experiment showing the titer of both phage and bacteria present in phage-infected mucosal epithelium, where exemplary microfluidic devices (chips) having the phage-infected mucosal epithelium were inoculated by introducing approximately $10^7$ bacteria into an input port, followed immediately by perfusion with phage- and bacteria-free media, and perfusion was continued for 18 hours to allow time for both the bacteria and phage to replicate within the mucus layer, as described in detail in Example 2, below.

We investigated the trilateral interactions between bacteria, phages, and mucosal epithelial cells using these chip microenvironments. For our model system we used mucus-producing human lung epithelial cells, T4 phages, and a T4 phage host, *Escherichia coli* B (*E. coli*). The phages included a mucus-adherent T4 phage (T4) and a T4 Hoc deletion mutant (T4Δhoc). T4Δhoc does not have the Hoc protein exposed on its capsid and does not adhere to mucus, but is otherwise a normal, infective T4 phage (15). To assay for antibacterial activity of the phages in the mucus layer, we perfused chips with media containing either T4 phage ($10^7$ $ml^{-1}$), T4Δhoc phage ($10^7$ $ml^{-1}$), or no phage for 24 hours to saturate the mucosal epithelium. Those phage that were not enmeshed within the mucus layer were removed by subsequent perfusion with phage-free media for one hour. We then inoculated each chip by introducing approximately $10^7$ bacteria into the input port, followed immediately by perfusion with phage- and bacteria-free media. Perfusion was continued for 18 hours to allow time for both the bacteria and phage to replicate within the mucus layer. We then scraped the mucus-covered epithelium from the glass and titered both the phage and the bacteria present (FIG. 1F). The continual fluid flow during these infection experiments allowed us to selectively observe bacterial and phage replication taking place within the mucus, as both the surrounding fluid and the sloughed mucus layers were continually washed away from the attached cells. Both the T4 and T4Δhoc phage populations actively infected and replicated in the *E. coli* present. Chips pretreated with T4 phage showed a significant antimicrobial effect, with a >4000-fold reduction in bacterial abundance compared to the no-phage control; the chips treated with T4Δhoc showed no significant difference from the no-phage control.

Figure 1G:
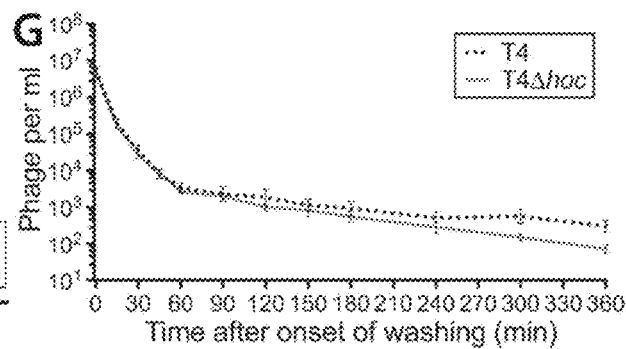
FIG. 1G graphically illustrates data from a Phage detachment experiment showing perfusion of exemplary microfluidic devices (chips) growing mucosal epithelium with either T4 or T4Δhoc phage ($10^7$ ml$^{-1}$) for 24 hours, after which they were perfused with phage-free media for six hours while phage detachment was monitored, as described in detail in Example 2, below.

Why did only the mucus-adherent T4 phage protect the in vitro epithelial surface from bacterial infection? Our initial BAM model proposed that the enrichment of phages in mucosal surfaces depended on the binding of the Ig-like Hoc proteins exposed on T4 phage capsids to mucin glycans (11). Thus the difference in antimicrobial effect observed here might be due to T4 phage accumulating to a higher abundance or persisting longer within the mucus layer. The first possibility was contradicted by the results of the previous experiment (FIG. 1F), with both phages accumulating to comparable abundance in the chips. To test the second, chips were perfused with either T4 or T4Δhoc phage ($10^7$ $ml^{-1}$) for 24 hours, after which they were perfused with phage-free media for six hours while phage detachment was monitored (FIG. 1G). Phage detachment was rapid during the first hour, with comparable numbers of T4 and T4Δhoc phage particles released. By this point, a large portion of the phage particles had already detached and the subsequent five hours showed the release of far fewer, with a slightly higher number of T4 phage particles recovered in the perfused media. Since T4 and T4Δhoc phage show the same patterns of accumulation and persistence on a life-like mucosal surface irrespective of Hoc-mediated adherence, some other mechanism must account for the observed disparity between their antibacterial effects. More generally, these observations indicate that phage abundance in mucus layers is governed by mucus secretion and turnover dynamics rather than by the ability of phages to adhere specifically to mucus.

Diffusion of Phages in Mucin Solutions.

Phages are inert particles dependent on random diffusion driven by Brownian motion to bring about their chance encounters with a bacterial host (16). Because of the key role of diffusion in phage reproductive success, we investigated the diffusive properties of T4 and T4Δhoc phage in mucus. Using high-speed multiple particle tracking (MPT) we observed the diffusion of both phage types across a range of physiological mucin concentrations: 0%, 0.2%, 0.6%, 1%, 2%, and 4% mucin in buffer (w/v), with 4% representing the highest concentration typically found in a mucosal layer (17). Fluorescence-labelled phage were mixed with a homogenous mucin solution in a well depression on a microscope slide and their diffusion was microscopically recorded at a temporal resolution of 43.5 ms. Individual phage particle trajectories were manually tracked and their effective diffusion constants ($\mu m^2/s$) calculated (FIG. 2A) (18).

The effective diffusion constant (K) of both phages were comparable in 0% mucin (buffer). Diffusion decreased with increasing mucin concentration for both phages, with T4 phage being slowed more markedly in 0.6% and 1% mucin than T4Δhoc phage. Specifically, diffusion of T4 phage was 21% less than T4Δhoc phage in 0.6% mucin and 29% less in 1% mucin. At 4% mucin, both phage particle types were effectively 'trapped' in the mucin solution. The higher temporal resolution and improved MPT methodologies employed here yielded lower diffusion constants than previously reported (11).

Subdiffusion of Mucus-Adherent Phages.

The diffusive movement of phages can be modeled as a random walk, where the calculated mean square displacement (MSD) of a phage particle represents the area 'explored' by the random walker. During normal, Brownian-driven diffusion, a particle's average position remains unchanged while its MSD increases linearly with time ($\tau$); that is, MSD ($\tau$)=K$\tau$. However, it is known that, within viscoelastic fluids and environments, diffusion can exhibit anomalous characteristics over time, being either enhanced (superdiffusion) or hindered (subdiffusion) (19, 20). Anomalous diffusion is characterized by a non-linear relationship between a particle's mean square displacement (MSD) and time ($\tau$) that can be expressed with the power law exponent alpha ($\alpha$), where MSD ($\tau$)=K$\tau^\alpha$ (21, 22). For normal diffusion $\alpha=1$, while superdiffusion is defined by $\alpha>1$ and subdiffusion by $\alpha<1$.

Figure 3A:
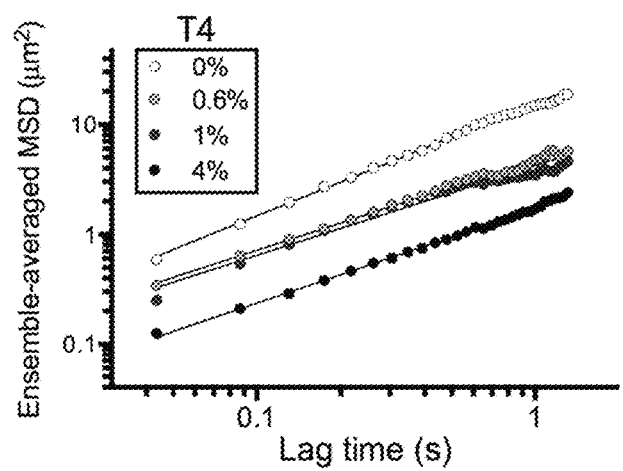
FIG. 3A-B graphically illustrates data where the measurement of ensemble-averaged mean square displacement (MSD) over time (lag time in seconds, or "s") was used to derived the values of a from the slope of the line of best fit for each phage-mucin combination T4 (FIG. 3A) and T4Δhoc (FIG. 3B) phage, as described in detail in Example 2, below.
Figure 3B:
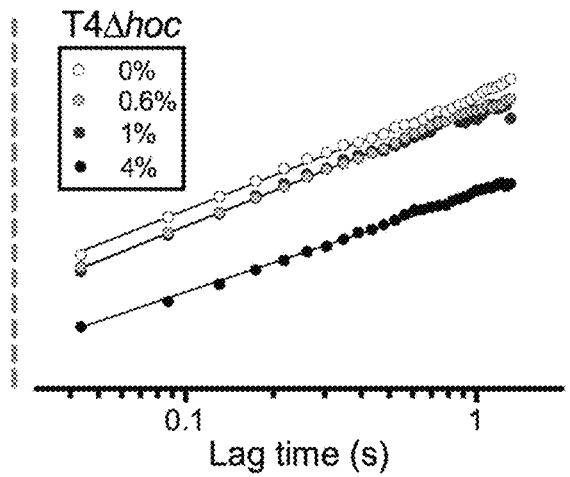

The effective diffusion constant (K) (FIG. 2A) and the diffusion exponent (a) are separate and independent phenomena in the sense that one cannot be taken as indicating the other. In order to investigate the nature of the observed diffusion of phage particles, we calculated the diffusion exponents ($\alpha$) from our MPT experiments for both phage types at all mucin concentrations (FIG. 2B). For this we measured the ensemble-averaged mean square displacement (MSD) over time and then derived the values of a from the slope of the line of best fit for each phage-mucin combination (FIG. 3). Both phages displayed normal diffusion (i.e., a is approximately equal to 1) in 0% mucin. As mucin concentrations increased, T4 phage showed a clear subdiffusive signal in 0.6% and 1% mucin solutions ($\alpha=0.82\pm0.02$ and $\alpha=0.82\pm0.01$, respectively), while T4Δhoc maintained normal diffusion ($\alpha=1.01\pm0.01$ and $\alpha=1.02\pm0.02$, respectively). At even higher mucin concentrations (4% mucin), both phage particle types showed a comparable subdiffusive signal ($\alpha=0.86\pm0.02$ and $\alpha=0.89\pm0.02$ for T4 and T4Δhoc phage, respectively).

This experimental system provides a much sought positive control for subdiffusion research that possesses two previously lacking properties: tunability and mechanism (23, 24). Tunability here is the ability to continuously adjust the mucin concentration and thereby effect a corresponding change in the degree of subdiffusion (the exponent $\alpha$). A potential mechanism is provided by the transient binding of the Hoc proteins covering the T4 phage capsids to the ubiquitous mucin glycans.

Theoretical Implications of Phage Subdiffusion in Mucus.

Subdiffusion has been observed in a wide variety of complex biological processes, including the intracellular transport of proteins and nucleic acids. In such situations, one might naïvely predict that the slower diffusion would slow vital processes as it might take longer for enzymes to 'find' substrates or for transcription factors to locate their DNA binding sites. Instead, subdiffusion has been shown to dramatically increase the rate of productive intracellular encounters (23, 25). This is attributed to the search dynamics of subdiffusive particles. These particles remain closer to their initial position during any interval of time, thereby exploring the local area more thoroughly than if moving by normal diffusion (19, 26).

Figure 4:
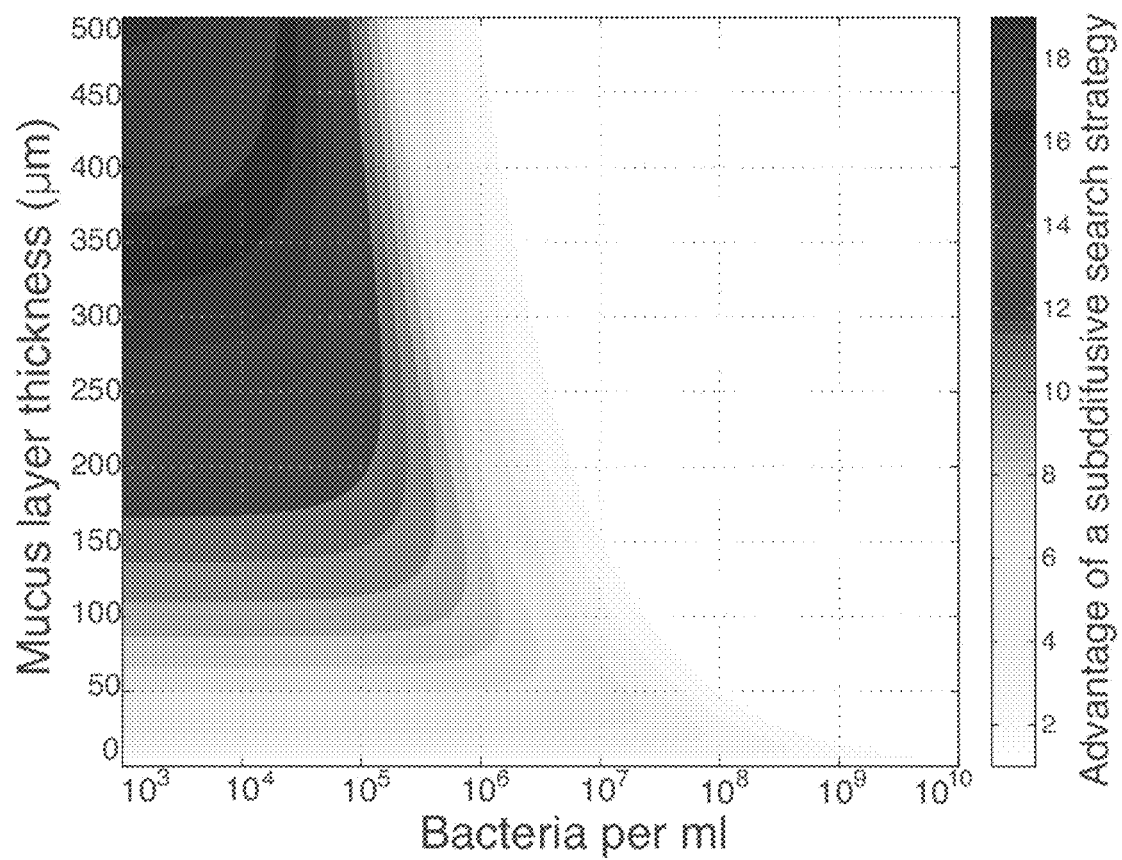
FIG. 4 graphically illustrates a color scale image showing the ratio of probabilities of bacterial encounter for a subdiffusive phage (α=0.82) versus a normally diffusing phage (α=1), where the ratio ranges from 19 (black) to 1 (white), as described in detail in Example 2, below.
Figure 7A:
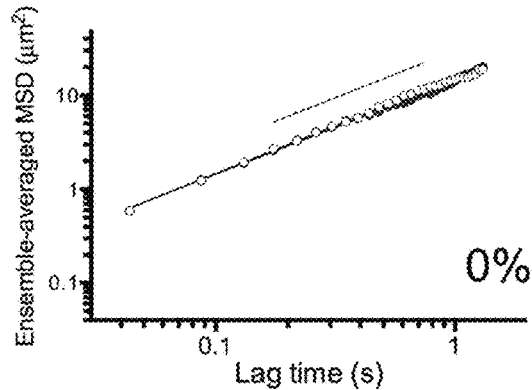
FIG. 7A-F graphically illustrates several Log-log graphs of the ensemble-averaged mean square displacement (MSD) (μm$^2$) of T4 and T4Δhoc phage in 0%, 0.2%, 0.6%, 1%, 2% and 4% mucin (w/v), as indicated in each panel, where solid lines indicate line of best fit from which the diffusion exponent (α) is determined, and the dashed line represents Brownian motion (α=1), as described in detail in Example 2, below.
Figure 7B:
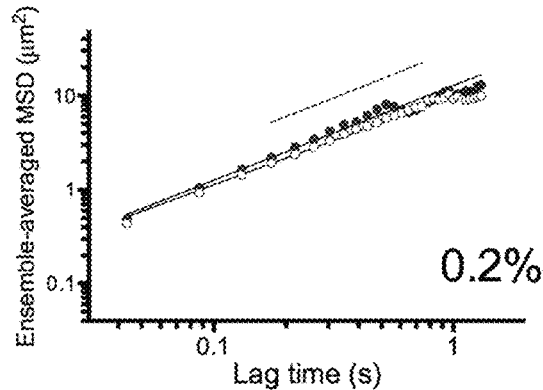
Figure 7C:
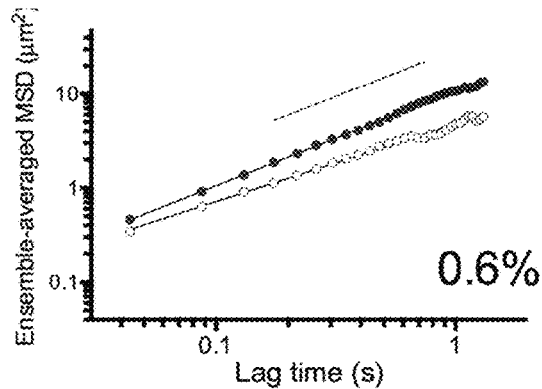
Figure 7D:
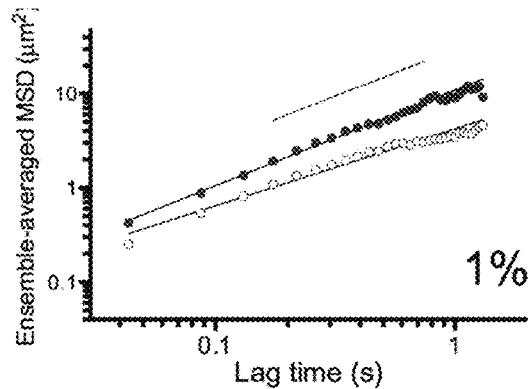
Figure 7E:
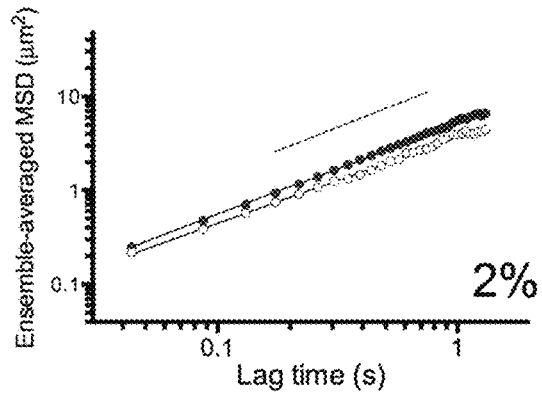
Figure 7F:
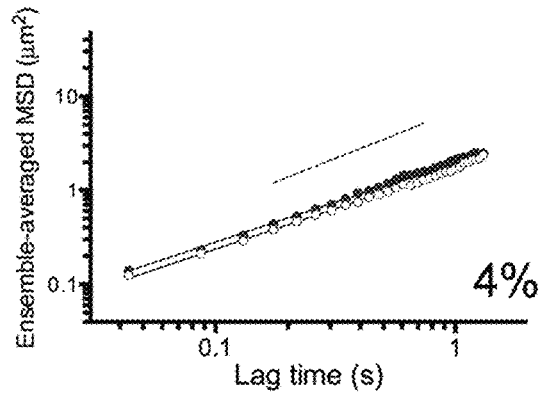

To consider the implications of subdiffusion for phages in mucus, we developed a simple model and compared the theoretical search efficiency for phage particles employing normal Brownian motion versus a subdiffusive search strategy (FIG. 4). Comparisons were made over a range of bacterial concentrations and mucus layer thicknesses, two factors that influence the likelihood that any phage particle will encounter a host bacterium before it leaves the mucus. Since increasing the bacterial concentration decreases the area a phage particle must search on average to locate a host, the frequency of phage-bacterial collisions rises with increasing bacterial concentration. The frequency of encounters also depends on the efficiency of the search strategy employed. Phage particles moving by subdiffusion search their local area more thoroughly independent of bacterial concentration. The other key factor is how long a phage particle remains in the bacteria-enriched mucus before it is sloughed or diffuses out of the mucus layer. The thicker the layer, the longer time on average that it will remain in the mucus, thus the more opportunities for collision with a potential host. The interplay of both of these factors with the diffusion exponent a predicts that a subdiffusive phage particle will explore the mucus layer more thoroughly and remain in the subdiffusive zone (see Discussion) longer than one moving by normal diffusion (FIG. 4). Further, the model predicts greater benefits of a subdiffusive search strategy at lower bacterial concentrations where phage-bacterial collisions are rare (26, 27). At high bacterial concentrations where collisions are frequent, more efficient searching by subdiffusion motion is expected to have little effect. Likewise, with thin mucus layers, both subdiffusive and normally diffusive phage particles would be quickly lost from the mucus.

Experimental Verification of Benefit of a Subdiffusive Search Strategy.

A major challenge in interpreting observations of subdiffusive motion in biological systems is the experimental demonstration of a conferred benefit (23). Here we used the classical adsorption assay (16, 28, 29) to test whether subdiffusion of T4 phage enhanced their rate of adsorption to bacterial hosts. We compared adsorption of T4 and T4Δhoc phage under conditions where our model predicted a subdiffusive search would be beneficial, i.e., low bacterial densities in 1% mucin. Experimental conditions were selected based on the previously determined adsorption constant of T4 and other T-even phages: $2.4 \times 10^{-9}$ ml/min (29). Either T4 or T4Δhoc phage was added to control (0%) or 1% mucin solutions containing $E.\ coli$ to give a final concentration of $2 \times 10^5$ phage particles $ml^{-1}$ and $1 \times 10^7$ bacteria $ml^{-1}$. At these concentrations, approximately 22% of phage particles were predicted to adsorb to a bacterial host over a 10-minute period. The suspensions were sampled every two minutes. Chloroform was immediately added to each sample to rapidly destroy all the bacterial cells and halt phage adsorption. The number of free phage particles in each sample was counted and used to calculate the adsorption constant (k) of T4 and T4Δhoc phage in both 1% mucin and control solutions (30). The adsorption of T4 phage was significantly higher in the 1% mucin solution (k=$4.7 \times 10^{-9}$ ml/min; n=6, t=−4.2, P<0.001) than in the control (k=$2.3 \times 10^{-9}$ ml/min; FIG. 5A). In contrast, there was no significant difference in the adsorption of the T4Δhoc phage between the 1% mucin (k=$2.6 \times 10^{-9}$ ml/min; n=6, t=−1.2, P=0.22) and the control (k=$2.1 \times 10^{-9}$ ml/min; FIG. 5B). Because our model predicted that the benefit of a subdiffusive search strategy would decrease with increasing bacterial concentration, we repeated these adsorption assays at a higher bacterial density ($7 \times 10^7$ $ml^{-1}$) where approximately 80% of phage particles were predicted to adsorb over a 10-minute period. Here neither T4 nor T4Δhoc phage showed enhanced adsorption in 1% mucin (Fig. S2).

Discussion

The search for a specific target is a ubiquitous process throughout biology. At the microscopic scale, molecules such as enzymes and repressor proteins perform site-specific searches within a cell; at the macroscopic scale, animals search for food (26, 31). Many predators possess prior knowledge of where prey are located, and can also utilize their senses to further direct their movement when hunting. For phages, the search for a susceptible bacterial host is effectively 'blind'. When limited to random searching, the chance for a successful encounter depends largely on the search strategy employed (32). In this situation, many motile predators, ranging from microbes to humans, use Levy flight, a superdiffusive search strategy, to increase their success (33-35). To the best of our knowledge, no organism has been shown to utilize a subdiffusive search strategy to the same effect. Phage particles, being inanimate and small (capsid diameters approximately 20-200 nm) act as colloidal particles subject to Brownian motion. Our study shows that the mucus-adherent T4 phage utilizes a subdiffusive search strategy in mucus that increases the frequency of host encounters.

Earlier work had predicted interactions between the T4 phage Hoc protein and mammalian organisms (36, 37). Subsequently we demonstrated that the Hoc proteins exposed on the T4 capsid bind to the mucin glycoproteins (11). The Hoc-bearing phages were enriched in mucus, reduced the bacterial load, and protected the underlying epithelial cells from infection, effects that we attributed to the putative mucin-binding activity of the Hoc protein (11). However, T4 and T4Δhoc phage particles also carry different capsid charges, as evidenced by their different electrophoretic mobilities (38). We cannot currently rule out the possibility that the observed BAM effects are due to these charge differences rather than to Hoc binding to the mucins. But our previous results demonstrating high structural homology between the T4 Hoc protein and known glycan-binding proteins support the mucin-binding mechanism (11).

Our previous work using an in vitro model system could not show a statistical difference between T4 and T4Δhoc phage in either their adherence to mucus-producing cells or their antimicrobial effect (11). Here we compared their adherence using a life-like mucosal surface with fluid flow dynamics and found little difference in either their accumulation or their persistence in the mucosal surface. Therefore we revise our initial hypothesis—that phage enrichment in mucus occurs via binding interactions—and conclude that the mucus mesh traps both phage types comparably and that phage persistence in mucus is likely governed by mucus secretion and microbial infection dynamics. Regarding their antimicrobial effect, we report a >4000-fold greater effect for T4 phage than for T4Δhoc phage in a mucosal surface.

Based on integration of our previous and current research findings, we have incorporated subdiffusion into our proposed bacteriophage adherence to mucus (BAM) model of immunity. T4 phage with its glycan-binding Hoc proteins exploits the benefits of a subdiffusive search strategy under specific, physiologically relevant mucin concentrations. When moving by subdiffusion, during any time interval a T4 phage particle remains closer to its initial position and explores the immediate mucus network more thoroughly relative to normal diffusion. Subdiffusion of T4 phage particles, but not T4Δhoc particles, was observed in 0.2% to 1% (w/v) mucin. At these concentrations, transient binding to mucins slowed, but did not arrest, T4 phage particles and shifted their motion from normal Brownian motion to subdiffusion. Phage-host encounters assayed in vitro in 1% mucin increased at low, but not high, bacterial concentrations.

As mucin concentration increases (e.g., 4% mucin), the mesh size of the mucin network decreases, likely approaching the capsid diameters of both phage types. As a result, the dense mucus network elicits subdiffusion of both phages, a phenomenon known to occur with particles in viscoelastic fluids such as mucus (39, 40). Subdiffusion at high mucin concentration is accompanied by very restricted diffusivity of both T4 and T4Δhoc phage particles, which masks the differential effect of transient mucin binding by T4 phage particles. Subdiffusion under these conditions is not predicted to benefit phages.

According to our current BAM model, a mucus-adherent phage particle that diffuses into a mucosal surface first encounters the region with the lowest mucin concentration and the most open mucin mesh. If it diffuses closer to the epithelium, mucin concentration increases and its diffusivity decreases. At the critical concentration, diffusion of these particles transitions to subdiffusion. More particles diffuse from the outer region into this subdiffusive zone per unit time than diffuse back out, resulting in their accumulation here (FIG. 6A). Those that diffuse still closer to the epithelium may become temporarily trapped in the more concentrated mucus, but the outward flux of the secreted mucins eventually carries them back into the subdiffusive zone. Within this zone, only the mucus-adherent phage particles transiently bind the mucin network, and this induces the subdiffusive motion that allows them to search the network more thoroughly. When a resultant phage-host encounter leads to a productive lytic infection, subdiffusion keeps the progeny particles released by host lysis within this zone longer. These two factors contribute to the increase in phage-host encounters that was observed in vitro at low bacterial concentration. However, as the concentration of bacteria increases, so does the chance of random phage-host encounters (29, 41). These encounters become so frequent that they mask the benefit provided by a subdiffusive search strategy that was evident at lower bacterial density.

In vivo mucosal surfaces are undoubtedly more complex than our simulated mucus environments. When considering that the in vivo diversity of bacterial host and even greater diversity of phage strains lowers the probability of a successful phage-host encounter, the implications of a more effective search strategy become apparent. In addition the mucus layer contains a mix of macromolecules including mucin glycoproteins, other diverse proteins, DNA, and polysaccharides, all of which could be expected to affect phage diffusion. Mucosal surfaces, being exposed to the surrounding milieu, experience environmental fluxes that may affect mucus structure and phage particle diffusion. For example, viral production in coral mucus is tightly coupled to temperature and salinity (42, 43). Temperature, salinity, and pH all affect the attachment of Hoc proteins to the T4 capsid (38) and thus have the potential to alter both the subdiffusion of phage particles and the frequency of productive phage-host encounters. Alterations of these physical parameters are known to occur in diseased mucosal surfaces, e.g., the high mucin concentrations (>4% w/v) and acidified mucosa characteristic of cystic fibrosis (CF) (40, 44). Although numerous studies have documented the effective use of phage to treat CF-associated bacterial infections (45, 46), how physical and physiological changes in the lung might affect phage diffusion, the frequency of productive phage-host encounters, and bacterial infection dynamics remains to be determined.

Taken together, this suggests that a tightly regulated symbiosis between phages and their metazoan hosts helps metazoans sustain a healthy microbiome and curb disease at mucosal surfaces. Within this symbiosis, the glycan-binding proteins of some phages have been fine-tuned to provide a balance between the greater speed of normal Brownian diffusion and the more thorough local searching afforded by subdiffusive motion (FIG. 6B).

Subdiffusion of phage particles in mucus has important and previously unrecognized implications for phage therapy. We propose that a subdiffusive search strategy, enhanced by mucin binding, underlies the ability of T4 phage, in contrast to T4Δhoc, to reduce bacterial colonization of our mucus-producing epithelial surface on a chip. To date, this protection of an epithelial surface by phage has been demonstrated only for T4 phage, which carries the carbohydrate-binding, immunoglobulin-like (Ig-like) domains of its Hoc protein exposed on its capsid (11). Similar protein domains are encoded by approximately 25% of the known members of the predominant order of phages (Caudovirales) (47). Given the enormous diversity of phages associated with mucosal surfaces, we expect many will be found to use Ig-like proteins or other carbohydrate-adherent surface proteins to increase their replicative success via a subdiffusive search strategy (48-51). Furthermore, we speculate that their mucin-binding is finely-tuned to position the phage particles in the optimal mucus zone where their bacterial hosts reside, utilizing the more efficient subdiffusive search strategy.

Phage selection criteria for clinical mucosal phage therapy have been limited to host range, burst size, and growth kinetics—phage characteristics that do not necessarily correlate with in vivo efficacy. An increased understanding of the subdiffusive search strategy of mucus-adherent phages, combined with physiologically relevant in vitro testing using microfluidic chips, may enable sound prediction of in vivo phage efficacy. Such accurate predictions are essential for the selection or engineering of phages for consistent clinical success. Engineered phages displaying an assortment of BAM domains may allow for unprecedented control to concentrate phages within a mucosal zone that overlaps with bacterial host ranges, leading to personalized therapeutics for mucosal disease.

Materials and Methods

Bacteria Strains, Phage Stocks, Tissue Culture Cell Lines, and Growth Conditions.

*Escherichia coli* B strain HER 1024 was used for all experiments and was grown in LB (10 g tryptone, 5 g yeast extract, 10 g NaCl, in 1 L dH$_2$0) at 37° C. overnight with shaking. The T4 Hoc phage deletion mutant (T4Δhoc) were kindly supplied by Prof. Venigalla B. Rao, The Catholic University of America, Washington, D.C. (15). The human tumorigenic lung epithelial cell line A549 was obtained from the American Type Culture Collection (ATCC) and cultured in F12-K media with 10% FBS, and 100 μg·ml$^{-1}$ penicillin—streptomycin (PS). TC cells were grown in 50 ml Primaria Tissue Culture Flasks (Becton Dickinson) at 37° C. under 5% $CO_2$.

Microbial Assay of Chips.

T4 phages and *E. coli* B strain were used at a concentration of $1 \times 10^7$ plaque forming units (PFU) and colony forming units (CFU) ml$^{-1}$ respectively for all chip assays. Prior to all experiments, chips were perfused with antibiotic- and serum-free medium containing T4 phage for 12 h at a flow rate of 100 μl h$^{-1}$. For phage-free washes, chips were perfused with antibiotic- and serum-free medium, and effluent from chips was titered. For bacterial infection, chips were inoculated with *E. coli* followed by perfusion with antibiotic- and serum-free medium for 18 h. The intact mucosal cell layer was then scraped and bacteria and phage titered.

Multiple Particle Tracking (MPT).

5 μl of SYBR Gold-labeled phage suspension ($10^9$ PFU ml$^{-1}$) was added to 45 μl of either 0%, 0.2%, 0.6%, 1%, 2%, or 4% (w/v) of type II porcine gastric mucin (Sigma) solution in SM buffer supplemented with 1 mM of $MgSO_4$ and $CaCl_2$. Solutions were immediately visualized using an Applied Precision OMX structured illumination microscope at 100×(1.40 NA). Movies were captured using Deltavision OMX: 43.5 ms temporal resolution for 100 frames, with >10 analyses per sample. Trajectories were manually tracked in two dimensions using MTrackJ plugin for ImageJ (18) with approximately 30 particle trajectories recorded for every analyses. Particle frame number, track ID, x and y coordinate, and time were extracted and analyzed.

Phage Adsorption Assays.

Adsorption assays were performed in LB supplemented with 1 mM of $MgSO_4$ and $CaCl_2$ pre-warmed to 37° C., and 1% (w/v) type II porcine gastric mucin (Sigma). *E. coli* B cells ($1 \times 10^7$ CFU ml$^{-1}$) were added to adsorption tubes, vortexed and CFU titered on LB agar plates at 37° C. overnight to ensure accurate bacterial quantification. T4 and T4Δhoc phage ($2 \times 10^5$ PFU ml$^{-1}$) were added to respective tubes, immediately vortexed, and sampled without agitation every 2 min continuously for 10 min. Each phage-bacteria sample was added to another tube containing LB media saturated with chloroform, vortexed, and free phage quantified in duplicate by titering.

Phage Stock Preparation.

Phage T4 and T4 Hoc deletion mutant (T4Δhoc) were isolated from single plaques and propagated in *E. coli* broths. Phage liquid lysates were centrifuged at 2880 RCF to remove bacteria, and 0.1 volume of chloroform was added followed by vortex mixing. Lysates were centrifuged at 2880 RCF and supernatant was collected. Lysates were added to Amicon® Ultra-15 ml centrifugal filters (EMD Millipore) and washed with 4 volumes of SM buffer (100 mM NaCl, 8 mM $MgSO_4$, 50 mM TrisHCl, in $dH_2O$) at 2880 RCF. Cleaned phage lysates were titered by top agar assays and stored at 4° C., over chloroform.

Microfluidic Device Design and Fabrication.

Fabrication of the microfluidic device (chip) mold was motivated by previous lab-on-a-chip work (1-3). The microfluidic device (chip) was fabricated from polydimethylsiloxane (PDMS: Sylgard, Dow Corning) that was mixed at a ratio of 10:1.5 (w/w) PDMS to curing agent. PDMS polymer was centrifuged for 5 min at 2880 RCF followed by degassing in a vacuum pump manifold until all air bubbles were removed. Degassed PDMS polymer was then poured into pre-fabricated molds of the inverse chip design made from High-Strength Ultem ¼" (McMater-Carr) and cured at 90° C. for 1 h. PDMS chips were then cut out of molds and trimmed to a minimal size using a razor blade. Chips were washed in pentane with stirring for 2 h, followed by three 2 h washes in Acetone with stirring in order to remove uncured PDMS from chips. An 89 mm diameter TiN Coated Round Punch (Syneo) was used to bore holes in the chips for inlet and outlet ports. After holes were punched, Scotch™ tape was used to clean both sides of the chip. The PDMS chip and polysine coated glass slide (Fisher) were exposed to plasma generated by a plasma etcher (Technics series 85-RIE). The plasma-treated surfaces were then immediately placed in conformal contact, resulting in irreversible bonding of the PDMS chip to the glass slide. Microfluidic tubing (Microbore PTFE tubing, ID 0.022", OD 0.042", Cole-Parmer) was sterilized by flowing through 70% (v/v) ethanol and cleaned by flowing through F12-K tissue culture media. Bonded chips and tubing were ultraviolet (UV) light sterilized for 15 min and tubing connected to both inlet and outlet ports of chips. Fluid flow was driven by a ten-plex syringe pump (Cole-Parmer), using slip-tip syringes (Fisher) and steel hypodermic needles (23G, Becton-Dickinson).

Cell Culture and Seeding Chips.

Human lung epithelial cells (A549, ATCC) were cultured in F12-K media supplemented with 10% FBS, according to the manufacturer's protocols. The cells were maintained at 37° C. in a humidified incubator under 5% $CO_2$ in air. Lung cells were harvested with trypsin/EDTA solution (0.25%, Fisher), pelleted, and resuspended in tissue culture medium. Cells were seeded into chips at approximately $5 \times 10^5$ cells per cm$^2$ by gently pumping the cell suspension into the main channel using a sterile syringe. Cells were allowed to attach to the polysine-coated glass slide surface overnight at 37° C. in a humidified incubator under 5% $CO_2$. A multiplex syringe pump was then used to perfuse culture medium continuously through the chip microchannel at a constant flow rate (40 μl h$^{-1}$) for four days to ensure the establishment of an intact monolayer. After visual confirmation of an intact cell layer, flow rate was increased (100 μl h$^{-1}$) for three days and the flow-rate was maintained for all experiments.

Microbial Infection Assay of Chips.

T4 phage and *E. coli* B strain HER 1024 (4) were used at a concentration of $1 \times 10^7$ colony forming units (CFU) and plaque forming units (PFU) ml$^{-1}$ for all chip infection assays. A549 cell monolayers were cultured in chips for 7 days prior to all experiments to ensure a confluent and consistent cell monolayer with mucus secretion. For phage pretreatment, cell culture media and tubing was switched to antibiotic- and serum-free medium containing T4 phage ($1 \times 10^7$ PFU ml$^{-1}$) and perfused through chips for 12 h at a flow rate of 100 μl h$^{-1}$. For phage-free washes, cell culture media and tubing was again switched to antibiotic- and serum-free medium without phage and washed for 1 h at a flow rate of 100 μl h$^{-1}$. For bacterial infection, *E. coli* B ($1 \times 10^7$ CFU ml$^{-1}$) was inoculated into the inlet port, followed by perfusion with antibiotic- and serum-free medium for 18 h at a flow rate of 100 μl h$^{-1}$. After infection assay, the excess media was cleared from the microchannel by gentle aspiration. Inlet and outlet ports of the chips were cut off using a diamond scribe and an in-house designed PDMS cutting tool, resulting in a clean cut and break of the chip. The intact cell monolayer and mucosal surface was then scraped from the chips microchannel using a slip-tip syringe and steel hypodermic needle (30G, Becton-Dickinson). Bacteria and phage were titered by CFU and PFU respectively (5).

Phage Washout Assay of Chips.

A549 cell monolayers were cultured in chips for 7 days prior to all experiments to ensure a confluent and consistent cell monolayer with mucus secretion. For phage pretreatment, cell culture media and tubing was switched to antibiotic- and serum-free medium containing T4 phage ($1 \times 10^7$ PFU ml$^{-1}$) and perfused through chips for 12 h at a flow rate of 100 µl h$^{-1}$. For phage-free washes, cell culture media and tubing was again switched to antibiotic- and serum-free medium without phage and washed for 6 h at a flow rate of 100 µl h$^{-1}$. Effluent from the chips was collected over the 6 h period and titered for phages (5).

Multiple Particle Tracking (MPT).

Glass slides and cover slips were silanized with hexamethyldisilazane (HMDS, Sigma-Aldrich) to prevent phage adherence to glass. Slides were placed in a wide mouth glass jar and a few drops of HMDS were added. The jar was covered with aluminum foil and left in chemical fume hood overnight. Assays were performed in plastic well chambers mounted on glass microscope slides. Phage suspensions ($10^9$ PFU ml$^{-1}$) were stained with 1000×SYBR Gold for 3 h at 4° C. in the dark. Stained phage were then washed with 4 volumes of SM buffer using Amicon® Ultra-0.5 ml centrifugal filters (EMD Milipore) at 2880 RCF to remove residual SYBR Gold stain.

Phage Adsorption Assays.

A rate-limiting step in the phage life cycle is the extracellular search by a phage for a new bacterial host culminating in the irreversible adsorption of the phage to the bacterial surface (6, 7). Adsorption of phage particles in liquid culture depends on chance encounters with a host, and the rate at which these collisions occur can be calculated using the equations that describe Brownian motion of colloidal particles in a solution (7, 8). These equations include an adsorption constant (k) that is specific for a given phage-host pair and that, in turn, depends on the rate of phage diffusion, the size of the bacterial target site, and the likelihood of phage attachment upon collision (8). The adsorption constant of T4 and other T-even phages was empirically determined to be $2.4 \times 10^{-9}$ ml/min (8).

Here phage adsorption assays were based on the chloroform-lysis approach (9, 10), and performed at a low bacterial density ($1 \times 10^7$ CFU ml$^{-1}$) such that approximately 22% of phage would adsorb to a bacterial host over a 10 min period (FIG. 5), and repeated at higher bacterial concentration ($7 \times 10^7$ CFU ml$^{-1}$) such that approximately 80% of phage would adsorb (FIG. S1). Optimal titers were theoretically calculated using the formula $P = P_0 e^{-kBt}$ where $P_0$ is the initial phage concentration ($2 \times 10^5$ phage ml$^{-1}$), k is the T4 phage adsorption constant ($2.4 \times 10^{-9}$ ml/min), B is the bacterial concentration, and t is time in min (8). For the assays, the percentage free phage was calculated by dividing the phage concentrations at each time point by the y-intercept calculated as a function of time. Free phage counts were transformed using natural-log, and the slopes of the adsorption curves then determined as a function of time (9). Phage adsorption constants (k) were calculated as the inverse slope divided by the concentration of bacteria (B) present in the adsorption media (k=−slope/B).

Statistical Analysis.

For the phage therapy infection of the microfluidic chips, we used the nonparametric Wilcoxon rank sum test to evaluate differences in bacterial population per chip between the three treatments (T4, T4Δhoc, and Control; FIG. 1F). If a chip had more than one replicate measurement, the measurement average was used. The pairwise Wilcoxon test with a Bonferroni correction for multiple comparisons indicates there was a significant difference in bacterial population medians between T4 and Control chips (P-value is 0.018). There was also a significant difference in bacterial population medians between T4 and T4Δhoc chips (P-value is 0.0476), but not between the T4Δhoc and Control chips (P-value is≈1). The Wilcoxon rank sum test was a post-hoc test after finding a significant effect of the conditions on the bacterial populations per chip using the Kτ uskal-Wallis test (P-value is 0.01436). Similarly, the Wilcoxon rank sum test was used to test the differences in phage population medians between the two experiment treatments (T4, T4Δhoc), with no significant difference observed (P-value is 0.9048).

For the phage adsorption assay, there appear to be qualitative differences in phage decay patterns over time between T4 Control (n=7) and T4 1% mucin (n=8) assays (FIG. 5A). To test the difference in the slopes, the growth (decay) curves were modeled using a linear mixed model. The decay curve data represented the repeated measurements of free phage from the adsorption assays over time. The linear mixed-effects model allows us to make inferences about the fixed effects of the mean intercept and the common slope (or decay rate). The random effect for the intercept describes the shift in the intercept for each adsorption assay. The two treatments of T4 Control and 1% mucin are modeled using indicator variables. Here PFU$_{ij}$ is the measurement for assay i at time j, where i=1, . . . , M and j=1, . . . , M$_i$. For this experiment M=10 and all assays have the same time index in minutes (2, 4, 6, 8, and 10 min) so that M=5 measurements. The final model can be written as:

$$PFU_{ij} = \beta_0 + \beta_1 \text{Treatment}_{ij} + \beta_2 (\text{Time} - 6)_{ij} + \text{Treatment}_{ij} \beta_2 (\text{Time} - 6)_{ij} + u_{0i} + \varepsilon_{ij}$$

The fixed effects are represented by $\beta_0$, $\beta_1$, $\beta_2$, and $\beta_3$. The parameter $\beta_1$ represents the fixed effect associated with the two treatments (T4 Control vs. T4 1% mucin). We have centered the Time variable at 6 minutes. The random effects are represented $u_{0i}$ and $\varepsilon_{ij}$. The term $u_{0i}$ represents the random intercept associated with assay i and is assumed to be a mean zero variance $\sigma^2_{int}$ random variable. The $\varepsilon_{ij}$ are the residuals for assay i at time j and are assumed to be mean zero normal random variables. The residual variance can be assumed to be the same for both treatments, but we allow the residual variance to be different for each treatment. So the T4 Control has residual variance $\sigma^2_{control}$ and the T4 1% mucin has residual variance $\sigma^2_{mucin}$. The model was fit with the R function lme by Restricted Maximum Likelihood (REML). The summary of the fixed effects is given by:

Fixed effects:Free phage~Treatment×$I$(Time−6).

|  | Value | Std. Error | DF | t-value | P-value |
|---|---|---|---|---|---|
| (Intercept) | 0.8740000 | 0.016966962 | 42 | 51.51187 | 0.0000 |
| Treatment | −0.0920000 | 0.023666937 | 9 | −3.88728 | 0.0037 |
| I(Time − 6) | −0.0210000 | 0.002245296 | 42 | −9.35289 | 0.0000 |
| Treatment:I(Time − 6) | −0.0153333 | 0.003644993 | 42 | −4.20668 | 0.0001 |

The small P-value associated with the Treatment effect and Treatment by Time interaction indicates that the T4 Control and 1% mucin have significantly different decay patterns. The significant fixed effect of Treatment ($\beta_1$-hat=−0.09) indicates that the T4 1% mucin on average has a smaller relative free phage. However, the significant interaction ($\beta_3$-hat=−0.015) indicates that T4 1% mucin at earlier times could have on average larger relative free phage compared to the T4 Control at earlier times (i.e., the lines may cross).

A likelihood ratio test indicated that the random intercept should be included in the model (P-value <0.001). The final model, which allowed for the residual variance to be different for each treatment, was chosen based on the AIC model selection criterion. Examination of the final model summary and diagnostic plots indicated that the model assumptions were satisfied. The summary of the random effects is given by:

~1|Replicate      Random effects formula

|  | (Intercept) | Residual |
|---|---|---|
| Std. Dev | 0.03518146 | 0.04448268 |

Variance Function:
Structure: Different Standard Deviations Per Stratum

~1|Treatment      Formula

Parameter Estimates:

| 1 | 0 |
|---|---|
| 1.0000000 | 0.7138346 |

Similarly, to test the differences in free phage decay patterns over time between T4Δhoc Control (n=6) and T4Δhoc 1% mucin (n=6) treatments, a linear mixed model was fit to the data (FIG. 5B). There was no significant Treatment or Treatment by Time interaction effect observed for the T4Δhoc Control (t=−1.32752, P-value is 0.217) and 1% mucin treatments (t=−1.2373, P-value is 0.223). The summaries of the fixed and random effects are given below.

Linear mixed-effects model for T4 hoc⁻ phage treatments fit by REML

| AIC | BIC | logLik |
|---|---|---|
| −161.5926 | −148.2085 | 87.79631 |

~1|Replicate      Random effects formula

|  | (Intercept) | Residual |
|---|---|---|
| Std. Dev | 0.02693415 | 0.04126077 |

Variance Function:
Structure: Different Standard Deviations Per Stratum

~1|Treatment      Formula

Parameter Estimates:

| 1 | 0 |
|---|---|
| 1.0000000 | 0.5162273 |

Fixed effects:Free phage~Treatment×I(Time−6).

|  | Value | Std. Error | DF | t-value | P-value |
|---|---|---|---|---|---|
| (Intercept) | 0.8784000 | 0.012776429 | 41 | 68.75161 | 0.000 |
| Treatment | −0.0245915 | 0.018524435 | 9 | −1.32752 | 0.217 |
| I(Time − 6) | −0.0204000 | 0.001506133 | 41 | −13.54462 | 0.000 |
| Treatment:I(Time − 6) | −0.0038145 | 0.003082743 | 41 | −1.23738 | 0.223 |

Method for Improved Multiple Particle Tracking Accuracy.

We previously published effective diffusivity values of T4 and T4Δhoc phage in buffer and 1% (w/v) mucin solutions at a temporal resolution of 100 ms (11). Those values were approximately 3-fold higher than the effective diffusion constants ($\mu m^2/s$) reported here. This discrepancy is the result of two factors. First, the improved temporal resolution of phage MPT employed here (43.5 ms vs. 100 ms), allowed us to more accurately measure the trajectories of phage particles compared to our previously reported MPT measurements (11). Second, here we improved our particle detection and particle linking schemes by switching from automated tracking to manual tracking (12). The automated particle tracking program detected particles based on fluorescence intensity, a user-defined particle radius cutoff, and other parameters (13). The program then attempted to link these detected particles to the closest detected particle in the following frame within a user-defined radius. Due to the low signal-to-noise ratio of fluorescence-labeled phage particles in mucin solutions, the identification of false positive particles by the automated tracking program increased the probability of making a spurious link (14). Therefore, we switched here to a manual tracking program that allowed us to more accurately identify and link phage particles. This method required more time to analyze phage MPT data, but it greatly improved our particle detection, reduced spurious links between frames, and resulted in higher quality MPT data overall.

Reduction Method for Multiple Particle Trajectory Data.

Subdiffusive motion of a particle is marked by a characteristic dependence of the particle's mean squared spatial displacement (MSD) on the lag time ($\tau$) between measurements of the particle's spatial position. Typically:

$$MSD = K\tau^\alpha, \quad (Eq. 1)$$

in which (the scaling exponent)$\alpha<1$. Normal Brownian motion would obey the same rule with $\alpha=1$. In this case K is related to the standard diffusion constant D by the relation K=2 dD, where d is the number of spatial dimensions monitored in the MSD (Table. S1). In our case d=2. In the case $\alpha<1$ (subdiffusion), the same relation holds, with D now referred to as the generalized diffusion constant as its units are not standard.

The literature discusses several random walk models that exhibit subdiffusion ($\alpha<1$). There are, as well, two principal ways of extracting this feature from data representing trajectories of particles: time averaging and ensemble averaging (15). Two of the models, Obstructed Diffusion (OD) and Fractional Brownian Motion (fBm), are characterized by stationary distributions and are therefore described as weakly ergodic. The third model, Continuous Time Random Walk (CTRW), breaks weak ergodicity. A consequence of this break is that CTRW will reveal its subdiffusive character only under ensemble averaging.

Ideally the data should be analyzed using both techniques, as the absence of a subdiffusive signal under time averaging and its presence under ensemble averaging would point to CTRW as the most likely of the three models discussed (15). However, to successfully determine the presence or absence of a subdiffusive signal from the data by means of time averaging requires observation of individual tracks extending over many decades. In our case, only a small fraction of the tracks extend as far as two decades. For that reason we were forced to use only ensemble averaging. As a result, in those cases where we observe subdiffusion, we are unable, with the tracking data alone, to support one model over another. Nevertheless, we consider the CTRW mechanism, with its intermittent interruptions of free diffusion, to more accurately represent the actual motion of T4 phage in mucus concentrations between 0.2% and 1% (w/v).

Here we describe the form of the trajectory data that we collected and the manner in which the ensemble averaging is carried out. The clearest way to understand the "ensemble averaging" technique for extracting an experimental value for MSD(τ) from tracking data is to think of it as an estimate for the expectation of a random variable from a well-defined sampling experiment. For a fixed value of ti, the sampling experiment is defined in two stages: 1) choose a track at random from the ensemble, 2) choose a time interval ($t_0$, $t_0+\tau$) at random (uniformly) from the history of the track. Note that only one interval of lag time τ is chosen from the track. The value of the random variable S (squared displacement) is calculated as:

$$S = \Delta r(\tau)^2 = [x(t_0+\tau) - x(t_0)]^2 + [y(t_0+\tau) - y(t_0)]^2, \quad (\text{Eq. 2})$$

where (x(τ), y(τ)) describes the position of the particle at time t. The quantity of interest, whose value is to be estimated from the data, is the expectation of S:

$$MSD_{exact}(\tau) = E[S]. \quad (\text{Eq. 3})$$

The data comes in the form of a number of observed trajectories of differing durations. Each trajectory is the result of a discrete set of particle positions recorded as a sequence of consecutive frames extracted as a subset from a movie of 100 frames. An estimate of the above expectation is obtained as follows. Given a lag time τ, enumerate all of the tracks in the collected data that are long enough to contain a time interval of length τ: j=1, ..., M. Select a random interval of length τ from the history of each track j and evaluate the squared displacement as in Eq. 2. Let $$SD(\tau) = \{\Delta^{r_j}(\tau)^2 | j=1, \ldots, M\} \quad (\text{Eq. 4})$$

be the set of sampled squared displacements. The estimate of the expectation is then the mean of the sample:

$$MSD_{estim}(\tau) = \frac{1}{M} \sum_{1}^{M} \Delta r_j(\tau)^2, \quad (\text{Eq. 5})$$

where it should be noted that M actually depends on τ. Note that the appropriate estimate of the variation in this value is the standard error of the mean (SEM), $$SEM = \sqrt{\frac{Var[SD(\tau)]}{|M(\tau)|}}. \quad (\text{Eq. 6})$$

The task now is to match the observed estimates $MSD_{estim}$(τ) to the functional form $K\tau^\alpha$ in Eq. 1.

That is most conveniently done by a weighted least squares fit, in which the difference for each value of τ is scaled by SEM. Explicitly, the fit is accomplished by minimizing the following sum over the values of K and a:

$$\sum_\tau \frac{(MSD_{estim}(\tau) - K\tau^\alpha)^2 |M(\tau)|}{Var[SD(\tau)]}. \quad (\text{Eq. 7})$$

The sum should be over only those τ for which |M(τ)| is large enough that the error estimate in Eq. 5 is good. We require |M(τ)|≥30. This method allows a measure of the error in the estimate of a and K to be assessed by the following non-parametric bootstrap scheme. The second stage in the sampling experiment defined above is indifferent to the choice of time interval of lag τ chosen from each track. Consequently, the procedure for computing α can be repeated with many different such choices, producing a distribution of estimates for α and K obtained from the same set of trajectory data. The means and standard deviations from these distributions provide the interval estimates of α and K quoted in the text (Table. S2 & S3).

Results

Mechanism of Phage Subdiffusion in Mucus.

What might be the molecular mechanisms underlying this observed subdiffusion by phage particles in mucus? From the perspective of a phage diffusing within a mucus layer, the world is a three-dimensional mesh of seemingly boundlessly long cables made of large mucin glycoproteins, each with thousands of variable glycan chains attached. Here the diffusion of any phage is slowed by increasing mucin concentrations, but still remains normal Brownian diffusion, i.e., its MSD increases linearly with time. However, for a mucus adherent phage such as T4, an additional factor alters this normal motion within a range of mucin concentrations (0.6% to 1%). The T4 phage capsid is decorated with many copies of a glycan-binding protein, Hoc, that reversibly bind to one or more of the ubiquitous mucin glycans. This transient binding both slows the particle's diffusion and provides the mechanism underlying subdiffusion of phage particles in mucus. When not bound to mucin, these mucus-adherent particles diffuse normally through the relatively spacious mesh of the mucus network. However, at any point in time some of the particles adhere and remain resting for a random interval that can be quite long (15, 16). Only while freely moving do the particles contribute to the measured increase in the ensemble-averaged MSD with time. If resting times are long, then as time passes more particles adhere than release per unit time, thereby continually depleting the fraction of free phage particles. With progressively fewer particles free to move by normal diffusion, the rate of increase of the ensemble-averaged MSD declines, i.e., α<1 (FIG. 3, Fig. S1).

Our model predicts that subdiffusion would not be observed for the T4Δhoc phage, or for any other phage that is unable to adhere to mucins, when the mucin mesh size exceeds the phage particle size (e.g., 0.6% and 1%). With further increase in mucin concentration, the mesh size decreases. When the mucin mesh size approaches the size of the phage particles (e.g., 2% and 4%), the diffusion of both T4 and T4Δhoc phage is markedly slowed and becomes anomalous over time, with α<1. The subdiffusion observed in higher mucin concentration is a result of the complex spatial structure of the mucin mesh, a phenomenon known to occur in viscoelastic fluids (17-19).

These mucus layers offer bacteria both a structured habitat and nutrients, and are heavily colonized by bacterial symbionts (20, 21). We posit that the mucin mesh deflects, entangles, and adsorbs bacteria. As a result of these increased mucin-bacterial interactions, a phage particle binding a mucin strand has an increased chance of encountering a host bacterium. If a phage-host encounter results in adsorption and a productive lytic infection, the phage will replicate within the host and then lyse the cell. The progeny phage particles released, perhaps a hundred or more, in turn perform a subdiffusive search for a host in the local mucus network. As this process repeats, the number of phages present increases, and likewise the number resting, briefly bound to nearby mucin fibers. Bacteria that continually collide with the mucin net are increasingly likely to encounter the subdiffusive phage.

Model of Phage Subdiffusion in Mucus.

Here we describe a simple model that explains why a phage's subdiffusive search strategy is more effective than a Brownian search. We also explore how the magnitude of this advantage varies with changing bacterial concentration and mucus layer thickness (FIG. 4).

We consider one single phage and calculate the probability (p) that this phage encounters a bacterium before moving out of the mucus layer. First we assume that the layer thickness (L) and bacterial concentration (B) are both small. The probability is proportional to the time the phage spends in the mucus ($\tau_M$) and the bacterial concentration. However the product of these two factors ($\tau_M B$) is not dimensionless while the probability (p) is. Hence the full expression has to include the basic units of length and time that characterize the problem. The basic unit of length is the size of a bacterium. We will call this length unit a and set it equal to 1 μm. For the basic unit of time we use the average time ($\tau_v$) required for a phage to move a distance a. Using Eq. 1 we estimate these times as:

$$\tau_V = \left(\frac{a^2}{K}\right)^{1/\alpha} \quad \text{(Eq. 8)}$$

and $$\tau_M = \left(\frac{3L^2}{K}\right)^{1/\alpha} \quad \text{(Eq. 9)}$$

The factor of 3 in Eq. 9 is due to the fact that only motion perpendicular to the layer contributes to the phage escaping from the mucus layer. All in all, $$p = \frac{\tau_M}{\tau_V} B a^3 = \left(\frac{3L^2}{a^2}\right)^{1/\alpha} Ba^3 \quad \text{(Eq. 10)}$$

Note that p increases when a decreases, indicating that a phage moving subdiffusively (α<1) has a higher likelihood of capturing a bacterium than a phage moving by Brownian motion (α=1).

Eq. 10 does not hold when either the mucus layer thickness or bacterial concentration are large. After all, the probability has to go to one in the limit of large layer thickness and/or bacterial concentration. Instead of the simple argument above, we now give the full derivation of an equation for the probability (p), which holds for any L and B.

Imagine dividing the mucus layer into voxels of volume $a^3$. At any moment in time, the probability (f) that a specific voxel is occupied by a bacterium is given by, $$f = Ba \quad \text{(Eq. 11)}$$

Now consider a time interval $\tau_v$. The phage will spend this entire time interval in one of the voxels. It will catch one of the bacteria if that voxel happens to be occupied at that moment (so with probability f). If unsuccessful, it will spend another time interval $\tau_v$, in a voxel where it again has a probability f to catch one of the bacteria. Note that this second time interval can be spent in the same or in a different voxel. This process is repeated N times before the phage moves out of the mucus, where, $$N = \frac{\tau_M}{\tau_V} = \left(\frac{3L^2}{a^2}\right)^{1/\alpha} \quad \text{(Eq. 12)}$$

The probability that each of the N searches is unsuccessful equals $(1-f)^N$. Hence the probability (p) of bacterial capture:

$$p = 1 - (1-f)^N \quad \text{(Eq. 13)}$$

For small f, Eq. 13 becomes p≅Nf, which is equal to Eq. 10. To predict how advantageous a phage subdiffusive search strategy is we calculate the ratio of p values for subdiffusive phage (we use α=0.82, which is the value obtained from mucus-adherent T4 phage in 1% mucus concentration) and diffusive phage (α=1). The ratio is shown as a function of the layer thickness L and the concentration B (FIG. 4).

We see that for a given mucus layer thickness, the advantage of a phage subdiffusive search strategy decreases with increasing bacterial concentration. This is in agreement with the adsorption assays, where T4 phage has a significantly increased adsorption constant in 1% mucin compared to the control solution (0%) at low bacterial concentrations (FIG. 5A) but not at higher bacterial concentrations (Fig. S1).

That a molecule moving in a subdiffusive manner has a higher probability (p) to find its target than one moving by Brownian motion was noted by Golding et. al. (22) in the context of cellular reactions. These authors employ an argument based on a model introduced by Halford et al. (23) to show that a molecule has a probability;

$$p \approx \left(\frac{a}{r}\right)^{3-2/\alpha} \quad \text{(Eq. 14)}$$

to find a single fixed target in a region with volume $r^3$ (23). This expression for p is identical to Eq. 10 after substituting;

$$\tau_M = \left(\frac{r^2}{K}\right)^{1/\alpha} \quad \text{(Eq. 15)}$$

and $$B = \frac{1}{r^3} \quad \text{(Eq. 16)}$$

We were tempted to just quote the result of Golding et. al (22), but realized the derivation in their paper is based on the fBm model of subdiffusion, known to be important in the crowded intracellular environments in which cellular processes occur. We suspect that mucus-adherent phages move in a CTRW subdiffusive manner due to the Hoc-mucin adherence mechanism and tunable subdiffusive motion in mucin concentrations between 0.6%-1% (w/v). Hence we needed to expand on the argument presented there, which we have done above. The difficulty with their argument is that the targets are taken to be static. With a static target a CTRW subdiffusive search cannot have an advantage over a search by normal Brownian motion. In CTRW motion the path followed by the hunting particle and hence the probability to visit the voxel containing the target is independent of $\alpha$. The subdiffusive character of the motion is due to particles getting stuck for time intervals that are distributed as $\tau^{-(1+\alpha)}$.

Our argument assumes only that the bacterial targets maintain a spatially uniform concentration during whatever motion they exhibit. The argument is therefore fully consistent with the CTRW mechanism. Finally, we point out that our model greatly simplifies a very complex situation. It neglects the fact that many phages with different host specificities are hunting in the mucus layer at the same time, and that they and their hosts may have different distributions. Moreover, it assumes a uniform bacterial density, while in fact both the bacteria and phages may be localized at specific regions within the mucus layer. Nevertheless, the model is able to explain two of the experimental trends that we observe. First, that subdiffusion of T4 phage in mucus leads to increased encounters with bacterial hosts compared to Brownian motion. Second, that the subdiffusive advantage is greater at lower bacterial concentrations.

FIGURE LEGENDS

FIG. 1. Microfluidic devices (chips) simulating a life-like in vitro mucosal surface. (A) Schematic of chip design. (B) Mucus-producing lung tissue culture cells seeded into the main channel of a chip. (C) Tissue culture cells in the main channel following perfusion for seven days. (D) Multiplex syringe pump and scaffold perfusing nine chips simultaneously. (E) Close-up of a single chip bonded to a glass microscope slide with microfluidic tubing attached to the in and out ports. (F) Phage therapy experiment. Cell layers were pretreated with T4 or T4Δhoc phage for 12 h, washed for 1 h, and then inoculated with *E. coli*. Cells with mucus layer were harvested 18 h later and both the phages and bacteria present were titered (PFU and CFU). (G) Phage detachment. Cell layers were pretreated with T4 or T4Δhoc phage for 12 h and then washed with phage-free media for 6 h, during which time the number of released phage was monitored by titering (PFU).

FIG. 2. (A) Effective diffusion constants ($\mu m^2/s$) calculated at 43.5 ms time intervals for T4 and T4Δhoc phage in 0% (buffer), 0.2%, 0.6%, 1%, 2%, and 4% mucin solutions (w/v). (B) Diffusion exponents ($\alpha$) of T4 and T4Δhoc phage in 0% (buffer), 0.2%, 0.6%, 1%, 2%, and 4% mucin solutions (w/v). Brownian diffusion $\alpha \approx 1$, subdiffusion $\alpha < 1$.

FIG. 3. Log-log graph of the ensemble-averaged mean square displacement (MSD) ($\mu m^2$) of T4 and T4Δhoc phage in 0% (buffer), 0.6%, 1%, and 4% mucin solutions (w/v). Solid lines indicate line of best fit from which the diffusion exponent (a) is determined.

FIG. 4. Theoretical advantage of a phage-host encounter for a phage particle employing a subdiffusive search strategy compared to Brownian motion across a range of bacterial concentrations and mucus layer thickness. Color scale indicates the ratio of probabilities of bacterial encounter for a subdiffusive phage ($\alpha=0.82$) versus a normally diffusing phage ($\alpha=1$). The ratio ranges from 19 (black) to 1 (white).

FIG. 5. Adsorption assay measuring the percentage of free phage remaining over a 10 min period in control (0%) and 1% mucin solutions. Error bars show standard deviation (n=6). Theoretical values were calculated from the T4 phage adsorption constant (k)=2.4×10$^{-9}$ ml/min, phage concentration (2×10$^5$ ml$^{-1}$), and bacterial concentration (1×10$^7$ ml$^{-1}$). (A) T4 phage. (B) T4Δhoc phage.

FIG. 6. Bacteriophage adherence to mucus (BAM) model with subdiffusion. (A) The mucus layer is a dynamic gradient of mucin glycoproteins. Closer to the epithelium, the mucin concentration increases. The corresponding decrease in the mucin mesh size reduces phage diffusion constants. Subdiffusive motion of mucus-adherent phage particles at lower mucin concentrations enriches phage particles within an optimal zone of the mucus layer. Left panel: qualitative representations of the effective diffusion constant (K) (solid blue line) and diffusion exponent (a) (dashed black line) for T4 phage from FIG. 2. (B) Transient binding of mucus-adherent phage to mucin glycoproteins facilitates subdiffusive motion over a range of mucin concentrations present within a mucus layer.

FIG. 7, or FIG. S1. Log-log graphs of the ensemble-averaged mean square displacement (MSD) ($\mu m^2$) of T4 and T4Δhoc phage in 0%, 0.2%, 0.6%, 1%, 2% and 4% mucin (w/v). Solid lines indicate line of best fit from which the diffusion exponent (a) is determined. Dashed line represents Brownian motion ($\alpha=1$).

Figure 8A:
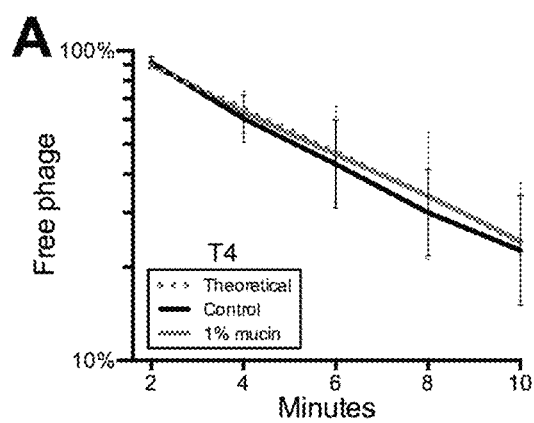
FIG. 8A-B graphically illustrates data from an adsorption assay measuring the percentage of free phage remaining over a 10 min period in control (0%) and 1% mucin solutions; the adsorption assays were performed at higher bacterial concentration such that approximately 80% of phage would adsorb to a bacterial host over the 10 min period, and theoretical values were calculated from the T4 phage adsorption constant (k)=2.4×10$^{-9}$ ml/min, phage concentration (2×10$^5$ ml$^{-1}$), and bacterial concentration (7×10$^7$ ml$^{-1}$)
Figure 8B:
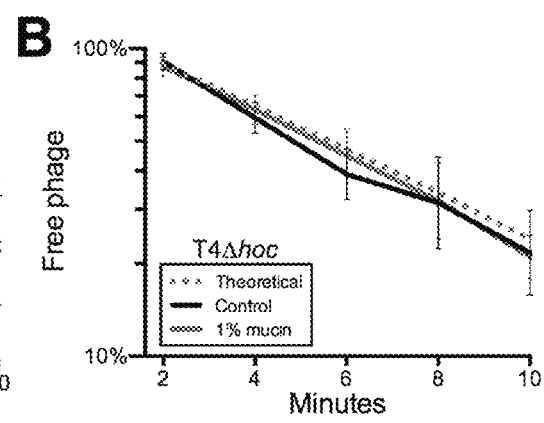

FIG. 8, or Fig. S2. Adsorption assay measuring the percentage of free phage remaining over a 10 min period in control (0%) and 1% mucin solutions. Error bars show standard deviation (n=4). Adsorption assays were performed at higher bacterial concentration such that approximately 80% of phage would adsorb to a bacterial host over the 10 min period. Theoretical values were calculated from the T4 phage adsorption constant (k)=2.4×10$^{-9}$ ml/min, phage concentration (2×10$^5$ ml$^{-1}$), and bacterial concentration (7×10$^7$ ml$^{-1}$). (A) T4 phage. (B) T4Δhoc phage.

Tables

TABLE S1

List of symbols used in calculations.

| Symbol | Definition |
|---|---|
| A | Size of a bacterium and voxel (a = 1 μm) |
| B | Bacterial concentration |
| d | Number of spatial dimensions |
| D | Standard diffusion constant |
| F | Probability that a specific voxel is occupied by one of the bacteria |
| k | T4 phage adsorption constant |
| K | Effective diffusion constant in MSD = $K\tau^\alpha$ |
| L | Thickness of the mucus layer |
| M(τ) | Number of trajectories that last a time τ or longer. |
| MSD | Mean Squared Displacement |
| n | Number of measurements |
| N | Number of voxels a phage searches before leaving the mucus layer |
| p | Probability that a phage encounters a bacterium before moving out of the mucus layer |
| P | Phage concentration |
| S | Squared displacement |
| SEM | Standard error of mean |
| t | Time |
| α | Diffusion exponent |
| Δr | Displacement |

TABLE S1-continued

List of symbols used in calculations.

| Symbol | Definition |
|---|---|
| $\tau$ | Time interval |
| $\tau_M$ | Average time a phage spends in the mucus layer |
| $\tau_V$ | Average time it takes a phage to cross a voxel |

TABLE S2

Mean and standard deviation of effective diffusion constants ($\mu m^2/s$) and diffusion exponent ($\alpha$) of T4 phage across all experimental conditions.
T4 Phage

| | Effective Diffusivity ($\mu m^2/s$) | | Diffusion Exponent ($\alpha$) | |
|---|---|---|---|---|
| Mucin % | Mean | St. Dev. | Mean | St. Dev. |
| 0% | 3.62 | 0.17 | 1.01 | 0.02 |
| 0.2% | 2.94 | 0.17 | 0.93 | 0.02 |
| 0.6% | 2.07 | 0.12 | 0.82 | 0.02 |
| 1% | 1.82 | 0.07 | 0.82 | 0.01 |
| 2% | 1.19 | 0.07 | 0.91 | 0.02 |
| 4% | 0.66 | 0.04 | 0.86 | 0.02 |

TABLE S3

Mean and standard deviation of effective diffusion constants ($\mu m^2/s$) and diffusion exponent ($\alpha$) of T4Δhoc phage across all experimental conditions.
T4Δhoc Phage

| | Effective Diffusivity ($\mu m^2/s$) | | Diffusion Exponent ($\alpha$) | |
|---|---|---|---|---|
| Mucin % | Mean | St. Dev. | Mean | St. Dev. |
| 0% | 3.64 | 0.24 | 0.99 | 0.03 |
| 0.2% | 3.14 | 0.27 | 0.99 | 0.04 |
| 0.6% | 2.63 | 0.11 | 1.01 | 0.02 |
| 1% | 2.54 | 0.14 | 1.02 | 0.02 |
| 2% | 1.37 | 0.07 | 0.99 | 0.02 |
| 4% | 0.74 | 0.04 | 0.89 | 0.02 |

REFERENCES

1. Johansson M E V et al. (2008) The inner of the two Muc2 mucin-dependent mucus layers in colon is devoid of bacteria. *Proc Natl Acad Sci USA* 105: 15064-9.
2. Linden S K, Sutton P, Karlsson N G, Korolik V, McGuckin M a (2008) Mucins in the mucosal barrier to infection. *Mucosal Immunol* 1:183-97.
3. d'Hérelle F (1921) *The bacteriophage: its role in immunity*. (Masson) Vol. 1.
4. Brüssow H (2005) Phage therapy: the *Escherichia coli* experience. *Microbiology* 151:2133-40.
5. Sulakvelidze A, Alavidze Z, Morris J G (2001) Bacteriophage therapy. *Antimicrob Agents Chemother* 45:649-59.
6. Chibani-Chennoufi S et al. (2004) In vitro and in vivo bacteriolytic activities of *Escherichia coli* phages: implications for phage therapy. *Antimicrob Agents Chemother* 48:2558-69.
7. Maura D et al. (2011) Intestinal colonization by enteroaggregative *Escherichia coli* supports long-term bacteriophage replication in mice. *Environ Microbiol*: 1-11.
8. Atuma C, Strugala V, Allen A, Holm L (2001) The adherent gastrointestinal mucus gel layer: thickness and physical state in vivo. *Am J Physiol Gastrointest Liver Physiol* 280:G922-929.
9. Lai S K et al. (2007) Rapid transport of large polymeric nanoparticles in fresh undiluted human mucus. *Proc Natl Acad Sci USA* 104:1482-7.
10. Johansson M E V, Larsson JMH, Hansson G C (2011) The two mucus layers of colon are organized by the MUC2 mucin, whereas the outer layer is a legislator of host-microbial interactions. *Proc Natl Acad Sci USA* 108 Suppl: 4659-65.
11. Barr J J et al. (2013) Bacteriophage adhering to mucus provide a non-host-derived immunity. *Proc Natl Acad Sci* 110:10771-10776.
12. Barr J J, Youle M, Rohwer F (2013) Innate and acquired bacteriophage-mediated immunity. *Bacteriophage*.
13. Kim H J, Huh D, Hamilton G, Ingber D E (2012) Human Gut-on-a-Chip inhabited by microbial flora that experiences intestinal peristalsis-like motions and flow. *Lab Chip*.
14. Ishikawa T, Sato T, Mohit G, Imai Y, Yamaguchi T (2011) Transport phenomena of microbial flora in the small intestine with peristalsis. *J Theor Biol* 279:63-73.
15. Fokine A et al. (2011) Structure of the three N-terminal immunoglobulin domains of the highly immunogenic outer capsid protein from a T4-like bacteriophage. *J Virol* 85:8141-8.
16. Schlesinger M (1932) Adsorption of phages to homologous bacteria. II. Quantitative investigations of adsorption velocity and saturation. Estimation of the particle size of the bacteriophage. *Z Hyg Infekt* 114:149-160.
17. Allen A, Flemstrom G, Garner A, Kivilaakso E (1993) Gastroduodenal mucosal protection. *Physiol Rev* 73:823-857.
18. Meijering E, Dzyubachyk O, Smal I (2012) Methods for cell and particle tracking. *Methods Enzymol* 504:183-200.
19. Guigas G, Weiss M (2008) Sampling the cell with anomalous diffusion—the discovery of slowness. *Biophys J* 94:90-4.
20. Saxton M J (2007) A biological interpretation of transient anomalous subdiffusion. I. Qualitative model. *Biophys J* 92:1178-91.
21. Barkai E, Garini Y, Metzler R (2012) Strange kinetics of single molecules in living cells. *Phys Today* 65:29.
22. Ernst D, Köhler J, Weiss M (2014) Probing the type of anomalous diffusion with single-particle tracking. *Phys Chem Chem Phys* 16:7686-91.
23. Höfling F, Franosch T (2013) Anomalous transport in the crowded world of biological cells. *Rep Prog Phys* 76:046602.
24. Saxton M J (2012) Wanted: a positive control for anomalous subdiffusion. *Biophys J* 103:2411-22.
25. Weiss M, Nilsson T (2004) In a mirror dimly: tracing the movements of molecules in living cells. *Trends Cell Biol* 14:267-73.
26. Golding I, Cox E (2006) Physical Nature of Bacterial Cytoplasm. *Phys Rev Lett* 96:098102.
27. Halford S E, Marko J F (2004) How do site-specific DNA-binding proteins find their targets? *Nucleic Acids Res* 32:3040-52.
28. Adams M H (1959) *Bacteriophages* (Interscience, New York, N.Y.).
29. Stent G S (1963) *Molecular biology of bacterial viruses* (Freeman and Company, San Francisco, Calif.).
30. Hyman P, Abedon S T (2009) *Practical methods for determining phage growth parameters* eds Clokie MRJ, Kτ opinski A M (Humana Press, Totowa, N.J.).
31. Sims D W et al. (2008) Scaling laws of marine predator search behaviour. *Nature* 451:1098-102.

32. Humphries N E, Weimerskirch H, Queiroz N, Southall E J, Sims D W (2012) Foraging success of biological Levy flights recorded in situ. *Proc Natl Acad Sci USA* 109: 7169-74.
33. Schuster F L, Levandowsky M (1996) Chemosensory Responses of *Acanthamoeba castellanii*: Visual Analysis of Random Movement and Responses to Chemical Signals. *J Eukaryot Microbiol* 43:150-158.
34. Raichlen D A et al. (2014) Evidence of Levy walk foraging patterns in human hunter-gatherers. *Proc Natl Acad Sci USA* 111:728-33.
35. Viswanathan G M et al. (1996) Levy flight search patterns of wandering albatrosses. *Nature* 381.
36. Dabrowska K, Switala-Jeleń K, Opolski A, Górski A (2006) Possible association between phages, Hoc protein, and the immune system. *Arch Virol* 151:209-15.
37. Dabrowska K et al. (2007) Hoc protein regulates the biological effects of T4 phage in mammals. *Arch Microbiol* 187:489-98.
38. Yamaguchi Y, Yanagida M (1980) Head shell protein hoc alters the surface charge of bacteriophage T4. *J Mol Biol* 141:175-193.
39. Lai S K, Wang Y-Y, Wirtz D, Hanes J (2009) Micro- and macrorheology of mucus. *Adv Drug Deliv Rev* 61:86-100.
40. Hill D B et al. (2014) A biophysical basis for mucus solids concentration as a candidate biomarker for airways disease. *PLoS One* 9:e87681.
41. Wiggins B A, Alexander M (1985) Minimum bacterial density for bacteriophage replication: implications for significance of bacteriophages in natural ecosystems. *Appl Envir Microbiol* 49:19-23.
42. Nguyen-Kim H et al. (2014) High occurrence of viruses in the mucus layer of scleractinian corals. *Environ Microbiol Rep*
43. Nguyen-Kim H et al. (2015) Coral mucus is a hot spot of viral infections. *Appl Environ Microbiol*: AEM.00542-15.
44. Pezzulo A A et al. (2012) Reduced airway surface pH impairs bacterial killing in the porcine cystic fibrosis lung. *Nature* 487:109-13.
45. James C E et al. (2015) Lytic activity by temperate phages of *Pseudomonas aeruginosa* in long-term cystic fibrosis chronic lung infections. *ISMS J* 9:1391-8.
46. Debarbieux L et al. (2010) Bacteriophages can treat and prevent *Pseudomonas aeruginosa* lung infections. *J Infect Dis* 201:1096-104.
47. Fraser J S, Yu Z, Maxwell K L, Davidson A R (2006) Ig-like domains on bacteriophages: a tale of promiscuity and deceit. *J Mol Biol* 359:496-507.
48. Dutilh B E et al. (2014) A highly abundant bacteriophage discovered in the unknown sequences of human faecal metagenomes. *Nat Commun* 5.
49. Tariq M A et al. (2015) A Metagenomic approach to characterize temperate bacteriophage populations from cystic fibrosis and non-cystic fibrosis bronchiectasis patients. *Front Microbiol* 6.
50. Abeles S R, Pride D T (2014) Molecular bases and role of viruses in the human microbiome. *J Mol Biol* 426: 3892-906.
51. Edlund A, Santiago-Rodriguez T M, Boehm T K, Pride D T (2015) Bacteriophage and their potential roles in the human oral cavity. *J Oral Microbiol* 7:27423.
1. Berthier E, Young E (2012) Engineers are from PDMS-land, Biologists are from Polystyrenia. *Lab Chip*.
2. Huh D et al. (2010) Reconstituting organ-level lung functions on a chip. *Science* 328:1662-8.
3. Kim H J, Huh D, Hamilton G, Ingber D E (2012) Human gut-on-a-chip inhabited by microbial flora that experiences intestinal peristalsis-like motions and flow. *Lab Chip* 12:2165-74.
4. *Escherichia coli* B strain HER 1024 Available at: http://www.phage.ulaval.ca/?pageDemandee=souche&noSouche=1024&id=42&L=1.
5. Protocol: Plating out phage (2011) Cent Phage Technol Texans A&M Univ.
6. Adams M H (1959) Bacteriophages (Interscience, New York, N.Y.).
7. Schlesinger M (1932) Adsorption of phages to homologous bacteria. II. Quantitative investigations of adsorption velocity and saturation. Estimation of the particle size of the bacteriophage. *Z Hyg Infekt* 114:149-160.
8. Stent G S (1963) Molecular biology of bacterial viruses (Freeman and Company, San Francisco, Calif.).
9. Hyman P, Abedon S T (2009) Practical methods for determining phage growth parameters eds Clokie MRJ, Kτ opinski A M (Humana Press, Totowa, N.J.).
10. Séchaud J, Kellenberger E (1956) Lyse précoce, provoquée par le chloroforme, chez les bactéries infectées par du bacteriophage. *Ann L Inst PASTEUR*, 90:102-106.
11. Barr J J et al. (2013) Bacteriophage adhering to mucus provide a non-host-derived immunity. *Proc Natl Acad Sci* 110:10771-10776.
12. Meijering E, Dzyubachyk O, Smal I (2012) Methods for cell and particle tracking. *Methods Enzymol* 504:183-200.
13. Sbalzarini I F, Koumoutsakos P (2005) Feature point tracking and trajectory analysis for video imaging in cell biology. *J Struct Biol* 151:182-95.
14. Chenouard N et al. (2014) Objective comparison of particle tracking methods. *Nat Methods* 11:281-9.
15. Ernst D, Köhler J, Weiss M (2014) Probing the type of anomalous diffusion with single-particle tracking. *Phys Chem Chem Phys* 16:7686-91.
16. Barkai E, Garini Y, Metzler R (2012) Strange kinetics of single molecules in living cells. *Phys Today* 65:29.
17. Mason T G, Ganesan K, van Zanten J H, Wirtz D, Kuo S C (1997) Particle Tracking Microrheology of Complex Fluids. *Phys Rev Lett* 79:3282-3285.
18. Mason T G (2000) Estimating the viscoelastic moduli of complex fluids using the generalized Stokes-Einstein equation. *Rheol Acta* 39:371-378.
19. Waigh T A (2005) Microrheology of complex fluids. *Reports Prog Phys* 68:685-742.
20. Backhed F, Ley R E, Sonnenburg J L, Peterson D A, Gordon J I (2005) Host-bacterial mutualism in the human intestine. *Science* 307:1915-20.
21. Martens E C, Chiang H C, Gordon J I (2008) Mucosal glycan foraging enhances fitness and transmission of a saccharolytic human gut bacterial symbiont. *Cell Host Microbe* 4:447-57.
22. Golding I, Cox E (2006) Physical Nature of Bacterial Cytoplasm. *Phys Rev Lett* 96:098102.
23. Halford S E, Marko J F (2004) How do site-specific DNA-binding proteins find their targets? *Nucleic Acids Res* 32:3040-52.

A number of embodiments of the invention have been described. Nevertheless, it will be understood that various modifications may be made without departing from the spirit and scope of the invention. Accordingly, other embodiments are within the scope of the following claims.

What is claimed is:

1. A genetically engineered bacteriophage of the genus *Caudovirales*, wherein the genetically engineered bacteriophage genome is altered such that after reproduction in a host cell, or in an in vitro system, the exterior or outer surface of the genetically engineered bacteriophage expresses or displays:
   (a) on a tailspike protein at least one non-bacteriophage carbohydrate binding domain (CBD) comprising a lectin;
   (b) at least one heterologous bacteriophage Ig-like CBD; or
   (c) a combination of (a) and (b).

2. The genetically engineered bacteriophage of claim 1, wherein the at least one non-bacteriophage carbohydrate binding domain (CBD) comprising a lectin, or the at least one heterologous bacteriophage Ig-like carbohydrate binding domain (CBD), is part of, or is attached to a tailspike protein of the genetically engineered bacteriophage.

3. The genetically engineered bacteriophage of claim 1, wherein the bacteriophage further comprises, or has contained within, or carries as a payload,
   a drug; an antibiotic; a bacteriostatic agent; a cytotoxic agent; a nucleic acid; a phage genome; an siRNA or antisense nucleic acid; a carbohydrate; a protein or peptide; a lipid; an antibody; a small molecule; a label or tag; a fluorescent molecule; a radiopaque molecule; a magnetic particle; a radionucleotide; a CBD; a moiety or domain capable of binding to: a protein or peptide, a nucleic acid, a lipid, a lipopolysaccharide or a mucopolysaccharide; or, any combination thereof.

4. The genetically engineered bacteriophage of claim 1,
   wherein the exterior or outer surface of the bacteriophage further comprises, or has attached to or has adherent to or carries a payload
   wherein optionally the payload comprises: a drug; an antibiotic; a bacteriostatic agent; a cytotoxic agent; a nucleic acid; a phage genome; an siRNA or antisense nucleic acid; a carbohydrate; a protein or peptide; a lipid; an antibody; a small molecule; a label or tag; a fluorescent molecule; a radiopaque molecule; a magnetic particle; a radionucleotide; a CBD; a moiety or domain capable of binding to: a protein or peptide, a nucleic acid wherein optionally the nucleic acid comprises an RNA or a DNA, a lipid, a lipopolysaccharide or a mucopolysaccharide; or, any combination thereof.

5. The genetically engineered bacteriophage of claim 1, wherein the genetically engineered bacteriophage comprises, or has attached to or has adherent to, or carries as a payload, between 1 and about 500 CBD molecules, or between about 10 and 400 CBD molecules, or between about 20 and 300 CBD molecules, or about 2, 5, 10, 15, 20, 25, 30, 35, 40, 50, 60, 70, 80, 90, 100, 110, 120, 130, 140 or 150 CBD molecules.

6. A composition comprising, or containing, or mixed with, or formulated with the genetically engineered bacteriophage of claim 1.

7. The composition of claim 6: formulated as or formulated for:
   (a) a capsule, a tablet, a gel, a geltab, a liquid, a solid, an elixir, a spray, a powder, a suppository or an implant, a sachet, a lozenge, a freeze-dried composition, or an infant formula,
   (b) a per dose, or per serving, or per unit dosage at, or a total daily dose of: between about 10(1) (or $10^1$) and 10(20) plaque-forming units (PFUs), or between about 10(3) and 10(17) PFUs, or between about 10(5) and 10(12) PFUs, or between about 10(7) and 10(9) PFUs,
   (c) administration in vivo; or for enteral or parenteral administration, or for ophthalmic, topical, oral, intravenous (IV), intramuscular (IM), intrathecal, subcutaneous (SC), intracerebral, epidural, intracranial or rectal administration, or by inhalation, or
   (d) a particle, a nanoparticle, a liposome, a tablet, a pill, a capsule, a gel, a geltab, a liquid, a powder, a suspension, a syrup, an emulsion, a lotion, an ointment, an aerosol, a spray, a lozenge, an ophthalmic preparation, an aqueous or a sterile or an injectable solution, a patch, an implant, a dietary supplement, an ice cream, an ice, a yogurt, a cheese, an infant formula or infant dietary supplement, a pasteurized milk or milk product or milk-comprising product.

8. The composition of claim 6, further comprising:
   a pharmaceutically acceptable excipient;
   a flavoring or a sweetening agent, an aspartamine, a stevia, monk fruit, a sucralose, a saccharin, a cyclamate, a xylitol, a vanilla, an artificial vanilla or chocolate or strawberry flavor, an artificial chocolate essence, or a mixture or combination thereof;
   a preservative, a benzoic acid, or a potassium sorbate;
   at least one probiotic or prebiotic, wherein optionally the prebiotic comprises an inulin, lactulose, extracts of artichoke, chicory root, oats, barley, various legumes, garlic, kale, beans or flacks or an herb;
   at least one congealing agent, wherein optionally the congealing agent comprises an arrowroot or a plant starch, a powdered flour, a powdered potato or potato starch, an absorbant polymer, an Absorbable Modified Polymer, and/or a corn flour or a corn starch;
   at least one an anti-inflammatory agent, wherein optionally the inflammatory agent comprises or is an NSAID, a 4 or a 5-amino-salicylate, an olsalazine, a mesalazine, a sulfasalazine and/or a balsalazide or an equivalent thereof or a combination thereof;
   an additive selected from one or more of a saline, a media, a defoaming agent, a surfactant agent, a lubricant, an acid neutralizer, a marker, a cell marker, a drug, an antibiotic, a contrast agent, a dispersal agent, a buffer or a buffering agent, a sweetening agent, a debittering agent, a flavoring agent, a pH stabilizer, an acidifying agent, a preservative, a desweetening agent and/or coloring agent, vitamin, mineral and/or dietary supplement, or a prebiotic nutrient; or
   an antacid,
   and optionally the buffer or a buffering agent or the pharmaceutically acceptable excipient comprises an inorganic salt, a citric acid, a sodium chloride, a potassium chloride, a sodium sulfate, a potassium nitrate, a sodium phosphate monobasic, a sodium phosphate dibasic or combinations thereof;
   and optionally the antacid comprises a calcium carbonate, a magnesium hydroxide, a magnesium oxide, a magnesium carbonate, an aluminum hydroxide, a sodium bicarbonate or a dihydroxyaluminum sodium carbonate; or
   any combination thereof.

9. The composition of claim 6, wherein the composition is formulated with or as: a delayed or gradual enteric release composition or formulation.

10. The genetically engineered bacteriophage of claim 1, wherein the at least one heterologous bacteriophage Ig-like CBD, or the at least one non-bacteriophage CBD comprising a lectin, binds to a mucus or mucus-like macromolecule, a mucin, a fatty acid, a phospholipid, a cholesterol, an elastin, a glycoprotein, a mucin glycoprotein or glycan, a mucin protein, a humic acid, a cellulose, a chitin, a high molecular weight (MW) polysaccharide, an N-acetylgalactosamine, an N-acetylglucosamine, a fucose, a galactose, a sialic acid or N-acetylneuraminic acid a mannose, or any combination thereof, and optionally the mucus is derived from: a mammalian mucus membrane, a gut, a urinary, a reproductive, an animal or an environmental mucus.

11. The genetically engineered bacteriophage of claim 1, wherein the at least one non-bacteriophage CBD comprising a lectin is a mammalian or a human CBD.

12. The genetically engineered bacteriophage of claim 10, wherein the mucus is or is derived from: a membrane, a gut, a urinary, a reproductive, a lung, a respiratory, an ocular, an oral, a nasal, a sinus, an oropharyngeal, a stomach, a small intestine, a large intestine, an enteric, a bowel, or a bladder mucus.

13. The genetically engineered bacteriophage of claim 10, wherein the mucus is derived from a coral, aquaculture, a dairy animal, a feed animal, a companion animal, a farm animal, a chicken, a cow, a sheep, a pig, a duck, a fish, a pet, a veterinary animal, a plants or an insect.

14. The genetically engineered bacteriophage of claim 1, wherein the at least one non-bacteriophage CBD is a mammalian or a human CBD.

15. The composition of claim 6, wherein the composition comprises or is coated with a gastro-resistant coating designed to dissolve at a pH of about 7 in the terminal ileum.

16. The composition of claim 6, wherein the composition comprises or is coated with an acrylic based resin or equivalent.

17. The composition of claim 16, wherein the resin or equivalent comprises a poly(meth)acrylate or a methacrylic acid copolymer B or NF.

18. A genetically engineered bacteriophage of the genus *Caudovirales*, wherein the genetically engineered bacteriophage genome is altered such that after reproduction in a host cell, or in an in vitro system, the exterior or outer surface of the genetically engineered bacteriophage expresses or displays:
  (a) at least one non-bacteriophage carbohydrate binding domain (CBD) comprising a C-type lectin;
  (b) at least one heterologous bacteriophage Ig-like CBD; or
  (c) a combination of (a) and (b).

\* \* \* \* \*